(12) United States Patent
Discenzo

(10) Patent No.: US 6,434,512 B1
(45) Date of Patent: Aug. 13, 2002

(54) MODULAR DATA COLLECTION AND ANALYSIS SYSTEM

(75) Inventor: Frederick M. Discenzo, Brecksville, OH (US)

(73) Assignee: Reliance Electric Technologies, LLC, Mayfield Heights, OH (US)

( * ) Notice: Subject to any disclaimer, the term of this patent is extended or adjusted under 35 U.S.C. 154(b) by 0 days.

(21) Appl. No.: 09/410,253

(22) Filed: Sep. 30, 1999

Related U.S. Application Data

(63) Continuation-in-part of application No. 09/300,645, filed on Apr. 27, 1999, and a continuation-in-part of application No. 09/257,680, filed on Feb. 25, 1999, and a continuation-in-part of application No. 09/257,785, filed on Feb. 22, 1999, which is a continuation-in-part of application No. 09/118,287, filed on Jul. 17, 1998, which is a continuation-in-part of application No. 09/054,117, filed on Apr. 2, 1998.

(51) Int. Cl.[7] .................................................. G06F 11/26
(52) U.S. Cl. ........................................ 702/184; 714/798
(58) Field of Search ................................. 702/183, 184, 702/185, 187, 188, 182; 714/100, 1, 25, 31, 37, 47, 48, 798; 700/3, 9, 19–21, 108, 109, 204, 258; 701/2, 24, 33, 29, 30

(56) References Cited

U.S. PATENT DOCUMENTS

| | | | | |
|---|---|---|---|---|
| 5,337,013 A | * | 8/1994 | Langer et al. ............... | 324/537 |
| 5,400,018 A | * | 3/1995 | Scholl et al. .......... | 340/825.54 |
| 5,481,906 A | * | 1/1996 | Nagayoshi et al. ........... | 73/116 |
| 5,566,091 A | * | 10/1996 | Schricker et al. ............. | 702/34 |
| 5,592,386 A | * | 1/1997 | Gaultier ....................... | 701/99 |
| 5,648,898 A | * | 7/1997 | Moore-McKee et al. ..... | 700/86 |
| 5,661,666 A | * | 8/1997 | Pawlak ........................ | 702/182 |
| 5,754,965 A | * | 5/1998 | Hagenbuch .................. | 701/35 |
| 5,925,817 A | * | 7/1999 | Kidokoro et al. ............... | 73/40 |
| 5,929,609 A | * | 7/1999 | Joy et al. ....................... | 322/25 |
| 6,006,146 A | * | 12/1999 | Usui et al. .................... | 701/29 |
| 6,128,560 A | * | 10/2000 | Ishii ............................. | 701/29 |
| 6,144,903 A | * | 10/2000 | Tousignant .................. | 701/29 |
| 6,157,894 A | * | 12/2000 | Hell et al. ..................... | 702/54 |
| 6,208,948 B1 | * | 3/2001 | Klinger et al. .............. | 702/183 |
| 6,230,089 B1 | * | 5/2001 | Lonn et al. .................... | 701/48 |
| 6,297,742 B1 | * | 10/2001 | Canada et al. .............. | 340/635 |
| 6,301,514 B1 | * | 10/2001 | Canada et al. .............. | 700/108 |

* cited by examiner

Primary Examiner—Marc S. Hoff
Assistant Examiner—Edward Raymond
(74) Attorney, Agent, or Firm—Himanshu S. Amin; William R. Walbrun; Alexander M. Gerasimow

(57) ABSTRACT

A diagnostics/prognostics system and related method for collecting and processing data relating to a plurality of subsystems of a dynamic system includes a plurality of sensors, each sensor gathering data and generating a data signal indicative of the health of a corresponding one of the subsystems. In addition, the diagnostics/prognostics system includes a plurality of subsystem modules coupled to corresponding ones of the sensors for generating a subsystem health signal in response to corresponding ones of the data signals. Further, a master diagnostics module is coupled to the subsystems to generate an overall system health signal in response to the subsystem health signals. Preferably, the master diagnostics module includes a memory having an embedded model to facilitate generating the overall system health signal and a related trend analysis. Preferably, a controller is used to generate a control signal in response to at least one of a group consisting of the subsystem health signals and the vehicle health signal, the control signal causing an operation parameter of at least one of the subsystems to change. The diagnostics/prognostics system is especially well suited for vehicles, but can also be applied to other dynamic systems.

44 Claims, 23 Drawing Sheets

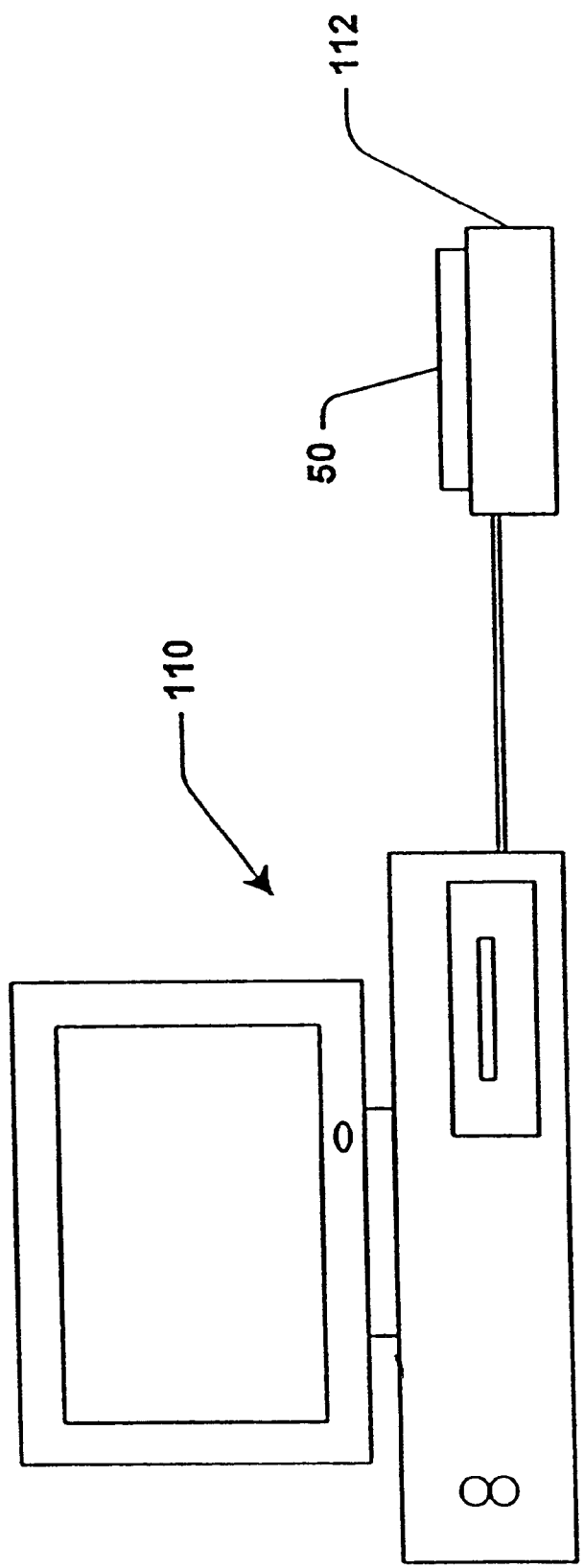

| $A_3$ | $A_{34}$ | $A_{56}$ | $A_{23}$ | $A_{67}$ | $A_{78}$ | $A_{234}$ | $A_{98}$ | $A_{26}$ | $A_4$ | $A_0$ | $A_{75}$ |
|---|---|---|---|---|---|---|---|---|---|---|---|
| $A_{34}$ | $A_{88}$ | $A_{45}$ | $A_{45}$ | $A_{36}$ | $A_{67}$ | $A_{27}$ | $A_{78}$ | $A_{96}$ | $A_{32}$ | $A_{16}$ | $A_{17}$ |
| $A_{57}$ | $A_{90}$ | $A_{45}$ | $A_7$ | $A_3$ | $A_{12}$ | $A_{478}$ | $A_{26}$ | $A_{83}$ | $A_{187}$ | $A_{73}$ | $A_{45}$ |
| $A_{78}$ | $A_{65}$ | $A_{56}$ | $A_{90}$ | $A_{45}$ | $A_{67}$ | $A_{24}$ | $A_{12}$ | $A_{56}$ | $A_{56}$ | $A_{76}$ | $A_{69}$ |
| $A_{84}$ | $A_{45}$ | $A_{78}$ | $A_{12}$ | $A_{47}$ | $A_{37}$ | $A_{127}$ | $A_{128}$ | $A_{234}$ | $A_{34}$ | $A_{33}$ | $A_{44}$ |
| • | • | • | • | • | • | • | • | • | • | • | • |
| • | • | • | • | • | • | • | • | • | • | • | • |
| • | • | • | • | • | • | • | • | • | • | • | • |
| $A_K$ | $A_H$ | $A_X$ | $A_Z$ | $A_X$ | $A_C$ | $A_Q$ | $A_B$ | $A_M$ | $A_1$ | $A_E$ | $A_Q$ |
| HEATHY MOTOR | HEATHY MOTOR | BAD BEARING | CRACKED ROTOR | INSULATION PROBLEM | HEATHY MOTOR | BAD BEARING | CRACKED CASING | LUBRICATION PROBLEM | BAD INNER RACE | BAD OUTER RACE | BAD BALL SURFACE |

FIG. 7

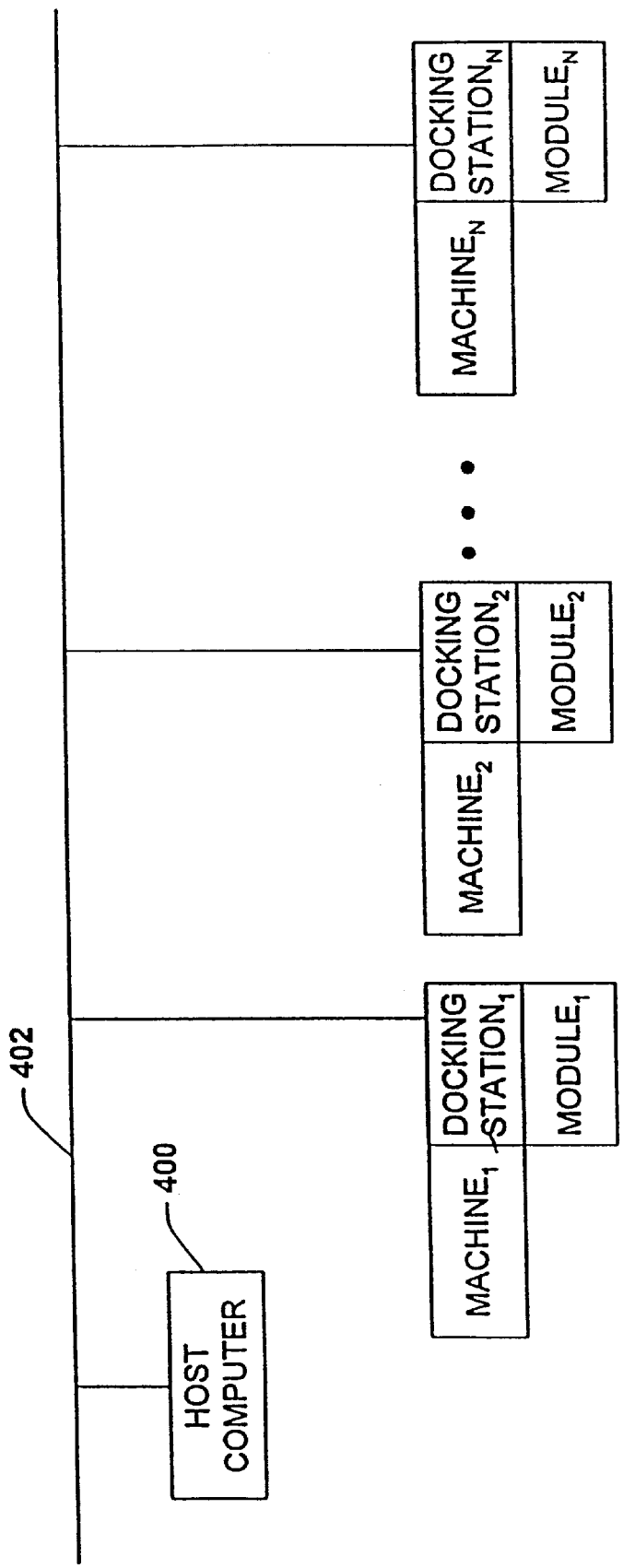

MODULAR DATA COLLECTION AND ANALYSIS SYSTEM

Cross Reference to a Related Application

This application is a continuation-in-part of U.S. patent application Ser. No. 09/118,287, filed Jul. 17, 1998, pending; U.S. patent application Ser. No. 09/300,645, filed Apr. 27, 1999, pending, which is a continuation-in-part of U.S. patent application Ser. No. 09/054,117, filed Apr. 2, 1998, pending; U.S. patent application Ser. No. 09/257,680, filed Feb. 25, 1999, pending, which is also a continuation-in-part of U.S. patent application Ser. No. 09/054,117, filed Apr. 2, 1998, pending; and U.S. patent application Ser. No. 09/257,785, filed Feb. 22, 1999.

BACKGROUND OF THE INVENTION a. Field of the Invention

The present invention relates generally to a data collection and analysis system for facilitating intelligent diagnostics and failure prevention.

b. Description of the Related Art

Dynamic systems such as transportation-systems and in particular vehicles are widely employed. In commercial settings, vehicles such as automobiles, trucks, buses, etc. are relied upon to operate with minimum maintenance over extended periods of time. For many businesses, a fleet of vehicles must be maintained and their usage coordinated for safe and efficient utilization of vehicle resources. For these businesses, downtime, and the random nature of it, is a significant concern. Likewise, passenger vehicles are also widely employed and, for consumers, these vehicles must be maintained to ensure driver and passenger safety.

Notably, such vehicles typically have a plurality of costly subsystems. In most vehicles, at least a small percentage of vehicle subsystems including lubrication, brakes, etc., are prone to failure at any time and, therefore, periodically require maintenance. Typically, maintenance is performed on a schedule (e.g., change the oil every 3,000 miles) without regard to the actual health status of the associated subsystem.

In addition to normal aging and use, failures due to poor or no maintenance and improper operation of the vehicle (e.g., "riding" the brakes, aggressive driving, etc.) take a significant toll on the vehicles, thus resulting in significant expense and logistical problems for the owner. Moreover, this problem is exacerbated when maintaining a large number of vehicles. As a result, a convenient yet inexpensive failure prediction system is desired.

Depending on the application, the failure of a vehicle in service can lead to overall system or process downtime, inconvenience, and potentially, the creation of a hazardous situation. Thus, it is desirable to monitor and diagnose potential failure or faults in these vehicle subsystems early in order to avoid such problems. Absent intelligent monitoring of the subsystems, these problems can have an insidious effect when a problem, although relatively minor and correctable if detected early, goes undetected and yields a set of circumstances that becomes more serious the longer the problem goes undetected. For example, steering and more general torque problems may not become apparent until irreversible damage has occurred. Likewise, problems due to inadequate lubrication, contamination or a multitude of other causes may not become apparent until the subsystems are damaged or a catastrophe occurs.

In order to reduce the probability of failure, preventive maintenance programs have been implemented in which vehicles are periodically serviced and routine maintenance is performed, while data regarding the general health and status of the vehicle is collected and recorded. By routinely conducting such preventive maintenance, vehicle subsystems are serviced whether or not such service is needed. This process results in vehicle downtime, significant costs and requires coordination of scheduled maintenance. Again, such problems are exacerbated when a plurality of vehicles, e.g., a fleet of commercial trucks, must be maintained. When maintenance is performed even though the actual health of the vehicle dictates that it is not necessary, overall process or system costs must be absorbed by the owner of the vehicles.

Moreover, often times no diagnostic or prognostic tests are performed as part of these routine service checks, relying instead on the driver or a maintenance specialist to detect fault conditions (e.g., via visual inspection, out-of-the-ordinary noises, etc.). Notwithstanding routine maintenance, often times unanticipated problems go unnoticed and ultimately develop into serious subsystem failures. Clearly, such a system is inefficient and, more importantly, places many of these vehicles at high risk of serious subsystem failure while in operation. This is a hazardous situation that should be avoided if at all way possible. Some on-board vehicle computer systems exist, but these systems are typically limited in scope and do not have the capability to analyze a comprehensive range of specific vehicle components (e.g., steering, brakes, fuel, etc.). In addition, no known system can efficiently detect early subsystem faults and failures or predict the time to failure. For example, some engine crankcase oil monitoring systems integrate time and temperature to determine if the oil needs to be replaced, but do not consider the effect of lubricant contaminants or multiple short cold running trips that never get the engine up to operating temperature.

Therefore, the field of vehicle diagnostics and maintenance systems is in need of an intelligent system that gathers real-time information relating to the health of a plurality specific vehicle subsystems to determine when maintenance is or will be required.

SUMMARY OF THE INVENTION

The present invention overcomes the limitations of prior vehicle diagnostic systems by providing a system of data collection and diagnostic/prognostic modules that collect data pertaining to vehicle subsystems and process the data to facilitate determining a health state of the individual subsystems, as well as a health state of the overall vehicle. The invention also can be utilized to predict trends in performance of the vehicle, thus affording the present system the ability to accurately and reliably predict when the next vehicle component/subsystem will fail. The system preferably includes a master diagnostics unit that is swappable and modular for rapid diagnosis of subsystem problems and efficient storage of vehicle maintenance records. These system features minimize vehicle downtime and maintenance costs without compromising vehicle performance and safety. In addition, by combining the results of subsystem analysis into an overall system (vehicle) model, the accuracy of the health assessment of individual subsystems may be improved. Also, system-level faults such as subsystem interaction problems and specific faults not previously defined may be detected.

More particularly, the subsystem modules are operatively coupled to components within each of the subsystems via an associated set of sensors. The sensors are positioned at suitable points within the subsystems to collect the desired data. The sensors are preferably intelligent sensors that are adaptable to different operating environments, such as those described hereinafter. The subsystem modules are, in turn, electrically coupled to a master diagnostic module that performs overall system health assessment. Because many of the sensors are placed substantially permanently within the components of corresponding subsystems, as are the subsystem modules, the master diagnostic module, in one preferred embodiment, can be quickly removed or inserted into a docking station mounted on the vehicle without having to worry about proper positioning of the sensors or their associated subsystem modules.

In operation, data is preferably collected, processed and stored by the individual subsystem modules, which themselves are capable of processing and diagnosing maintenance concerns in generating subsystem health assessment signals. The master diagnostics module receives the subsystem health assessment signals and, in response, generates and stores in a memory an overall vehicle health assessment. This memory is preferably sufficient to store a substantial amount of raw and/or processed data. As a result, the master diagnostics module may be employed to gather data for extended periods of time, for example, several weeks, several months or several years. Data collection for extended periods of time affords improved accuracy and machine diagnosis as well as substantially facilitating trend analysis of machine performance and failure prediction.

Furthermore, because the sensors are strategically disposed on or within the vehicle subsystems, and more particularly, the subsystem components, as compared to placing the sensors within the modules, the present invention provides for accurate and reliable data from which to base subsystem and overall vehicle diagnostics and trending.

Overall, the present invention permits a substantial portion of vehicle subsystem and overall vehicle diagnostic processing and analyses to be performed locally, i.e., on board. As a result, in at least one preferred embodiment, the amount of data that is sent to a remote computer for additional processing is minimized, thus reducing bandwidth and/or transmission time requirements for data transmission.

According to one aspect of the invention, a vehicle diagnostic system for collection of data relating to a plurality of subsystems of a vehicle includes a plurality of sensors, each sensor gathering data and generating a data signal indicative of the health of a corresponding one of the subsystems. In addition, the vehicle diagnostic system includes a plurality of subsystem modules each electrically coupled to corresponding ones of the sensors for generating a subsystem health assessment signal in response to corresponding ones of the data signals. The system further includes a master diagnostics module electrically coupled to the subsystem modules to generate an overall vehicle health signal. It may also use the inherent coupling of vehicle subsystems to further establish the health assessment of individual subsystems.

According to another aspect of the invention, a vehicle diagnostics/prognostics system for collecting and processing data relating to a plurality of subsystems of a vehicle includes a plurality of subsystem modules for receiving health assessment information associated with each of the subsystems and generating corresponding subsystem health signals based on the health assessment information. In addition, the system includes a master diagnostics module electrically coupled to the subsystem modules and including a memory having a health assessment model embedded in the memory, the master diagnostics module for generating a vehicle health assessment based on the health assessment model and in response to the subsystem health signals.

According to another aspect of the invention, the system includes a central terminal adapted to be communicably coupled to the master diagnostic module to facilitate further processing of the subsystem and overall vehicle health signals for generating maintenance schedules and trend analyses.

According to a still further aspect of the invention, the master diagnostics module is a plug-in module that is communicably coupled to the central terminal via a docking station situated at a location remote from the vehicle. Preferably, the central terminal includes a host computer to facilitate further diagnostics and trending processing.

According to another aspect of the invention, the master diagnostics module is communicably coupled to the central terminal via a wireless communications interface such as radio, digital cellular , paging network, etc.

According to yet another aspect of the invention, a method of determining when a vehicle requires maintenance includes the step of using a plurality of sensors to gather data indicative of the health of corresponding ones of a plurality of subsystems, and to generate corresponding data signals based on the health data. Further, the method includes the step of providing a plurality of subsystem modules each associated with a corresponding ones of the subsystems, each of the subsystem modules being electrically coupled to a corresponding one of the sensors. Next, the method includes the steps of generating, with the subsystem modules, subsystem health signals in response to corresponding ones of the data signals, providing a master diagnostics module electrically coupled to the subsystem modules, and generating, with the master diagnostics module and in response to the subsystem health signals, a vehicle health signal.

These and other objects, features and advantages of the present invention will be better appreciated and understood when considered in conjunction with the following description and accompanying drawings. It should be understood that the following description indicates one or more preferred embodiments of the present invention, but is given only to illustrate and not to limit the invention. Many changes and modifications may be made within the scope of the present invention without departing from the spirit thereof, and the invention includes all such modifications.

BRIEF DESCRIPTION OF THE DRAWINGS

A clear conception of the advantages, features, construction, and operation of the present invention will become more readily apparent by referring to the exemplary, and therefore nonlimiting embodiments illustrated in the drawings accompanying and forming a part of this specification, wherein like reference numerals designate the same elements in the several views and in which:

FIG. 3 is a front view of the data collection module connected to a docking port which is connected to the host computer in accordance with the present invention;

FIG. 5b is a graph of a Fast Fourier Transform signal representative of the instantaneous motor current signal of FIG. 5a;

FIG. 6b is a graph of a Fast Fourier Transform signal representative of the instantaneous motor current signal of FIG. 6a;

FIG. 7 is a table diagram of vibration amplitudes over a range of frequencies, which may be used to facilitate diagnosing the state of a dynamoelectric machine in accordance with the present invention;

FIG. 9 is a schematic illustration of a system for collecting diagnostic data for a plurality of machines in accordance with the present invention.

DETAILED DESCRIPTION OF THE PREFERRED EMBODIMENTS

A. Machinery Data Collection and Analysis System

For convenience, the contents of U.S. Ser. No. 09/118,287, upon which priority is claimed, is repeated below. The remainder of U.S. Ser. No. 09/118,287 that is not repeated below is hereby incorporated by reference.

The machinery data collection and analysis system relates to a system for conveniently and cost effectively obtaining and using data for machinery diagnosis and failure prediction. In particular, the system employs a self-contained, compact module which is coupleable to a docking station attached to a dynamoelectric machine. A plurality of sensors are suitably positioned within and about the machine to collect data. The sensors are operatively coupled to the docking station, and thus the module may collect the data by coupling to the docking station. The module is adapted to collect data for extended periods of time, and to process and store the data. It is to be appreciated that the machinery data collection and analysis system may be applied to most rotating machinery (e.g., motors, pumps, generators, gear boxes) and/or systems.

Figure 1:
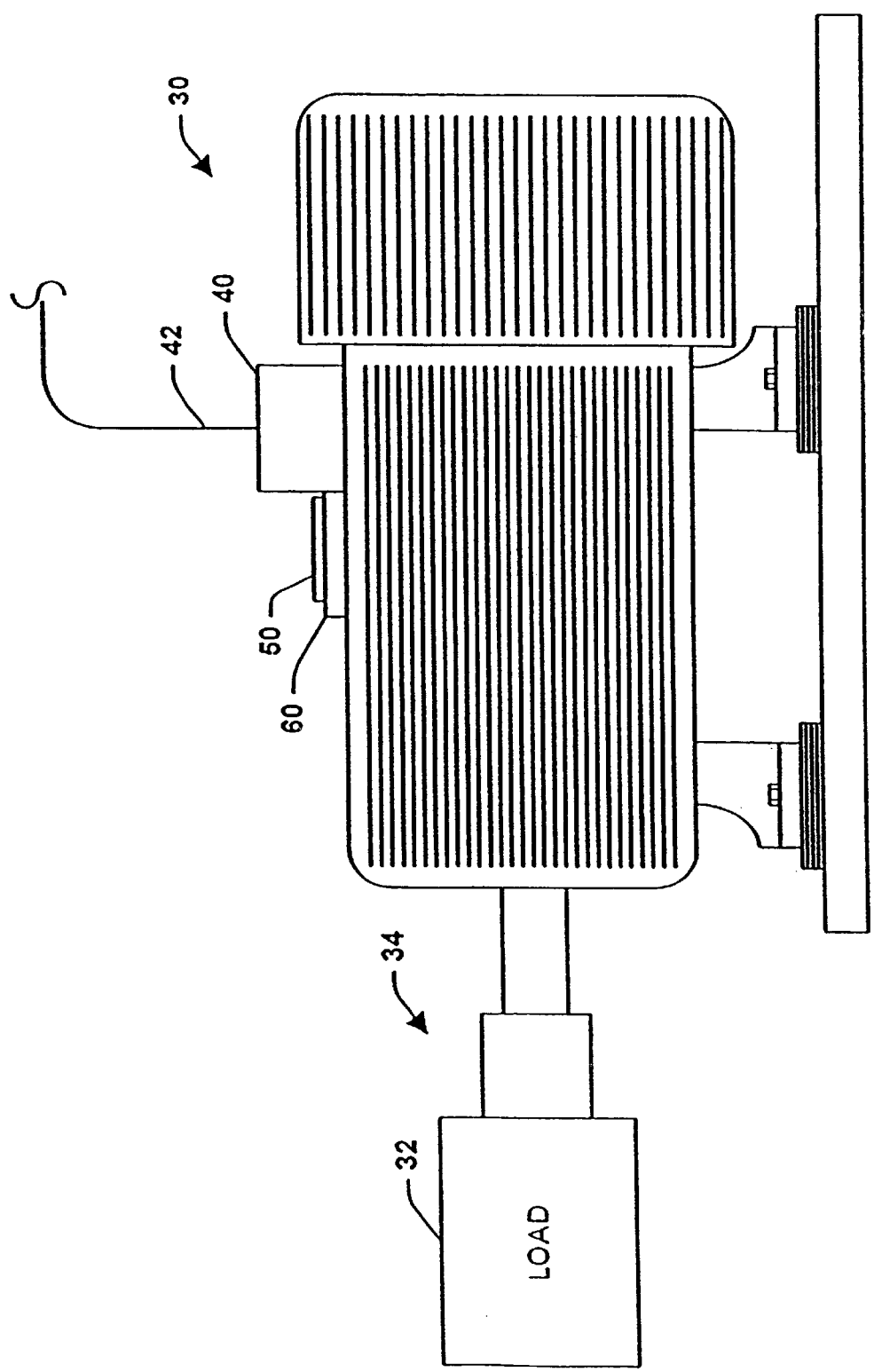
FIG. 1 is a side view of an integrated AC induction motor and data collection module in accordance with one particular aspect of the present invention.

Referring initially to FIG. 1, one specific environment in which the machinery data collection and analysis system may be employed is shown. A three-phase AC induction motor 30 is depicted driving a load 32 through a shaft coupling 34. The motor 30 includes a junction box 40 for receiving conductors from power lines via a conduit 42. The motor 30 is AC powered and operates at an AC power line frequency of 60 Hz. However, it is appreciated that different line frequencies (e.g., 50 Hz.) may be employed. A diagnostic module 50 is operatively coupled to the motor 30 via a docking station 60. As will be discussed in greater detail below, various sensors 62 (e.g., accelerometers, thermocouples, optical sensors, temperature sensors, encoders, viscosity sensors, flux sensors) (see FIG. 4a) are strategically positioned within and/or about the motor 30 to collect desired data. These sensors 62 are also coupled to the docking station 60. Thus, the diagnostic module 50 collects and analyzes raw motor data collected from within the motor 30 via the sensors 62. As a result of employing the certain sensors 62 (e.g., accelerometers, encoders, thermocouples, temperature detectors, viscosity sensors, flux sensors) internal to the motor, the data being analyzed is highly accurate and affords for making accurate and reliable determinations relating to the performance and health of the motor 30, future health of the motor 30, and health and future health of a process employing the motor 30.

The docking station 60 facilitates providing certain sensors internal to the motor 30. Some conventional data collection devices mount to the motors but since they do not employ docking stations, the sensors of such devices typically are provided within the data collection itself. Consequently, such conventional data collection devices are inferior to the preferred collection and analysis system at least with respect to the quality of the data collected. More particularly, the quality of data collected from sensors external to the motor will be less than the quality of data collected by sensors internal to the motor. The preferred collection and analysis system affords for suitably positioning sensors 62 internal to the motor 30. Sensors placed internal to the motor 30 may be strategically located where sensed information is closely related to the health of the motor. External sensors will sense information which includes the affects of thermal conductivity, separating material, and related reflected and diffused a sensed values.

The docking station 60 further provides for the sensors 62 to be permanently positioned at desired optimal locations.

Conventional data collection devices are removed periodically from the machine from which data is being gathered, and subsequent monitoring requires an attempt to reposition the conventional data collection device at roughly the same position on the machine as it was previously placed. Such consistent repositioning oftentimes does not occur resulting in inconsistent placement of the sensors within the conventional data collection devices with respect to the machine being measured. The machinery data collection and analysis system via the docking station 60 mitigates this deficiency of conventional data collection devices.

Figure 2:
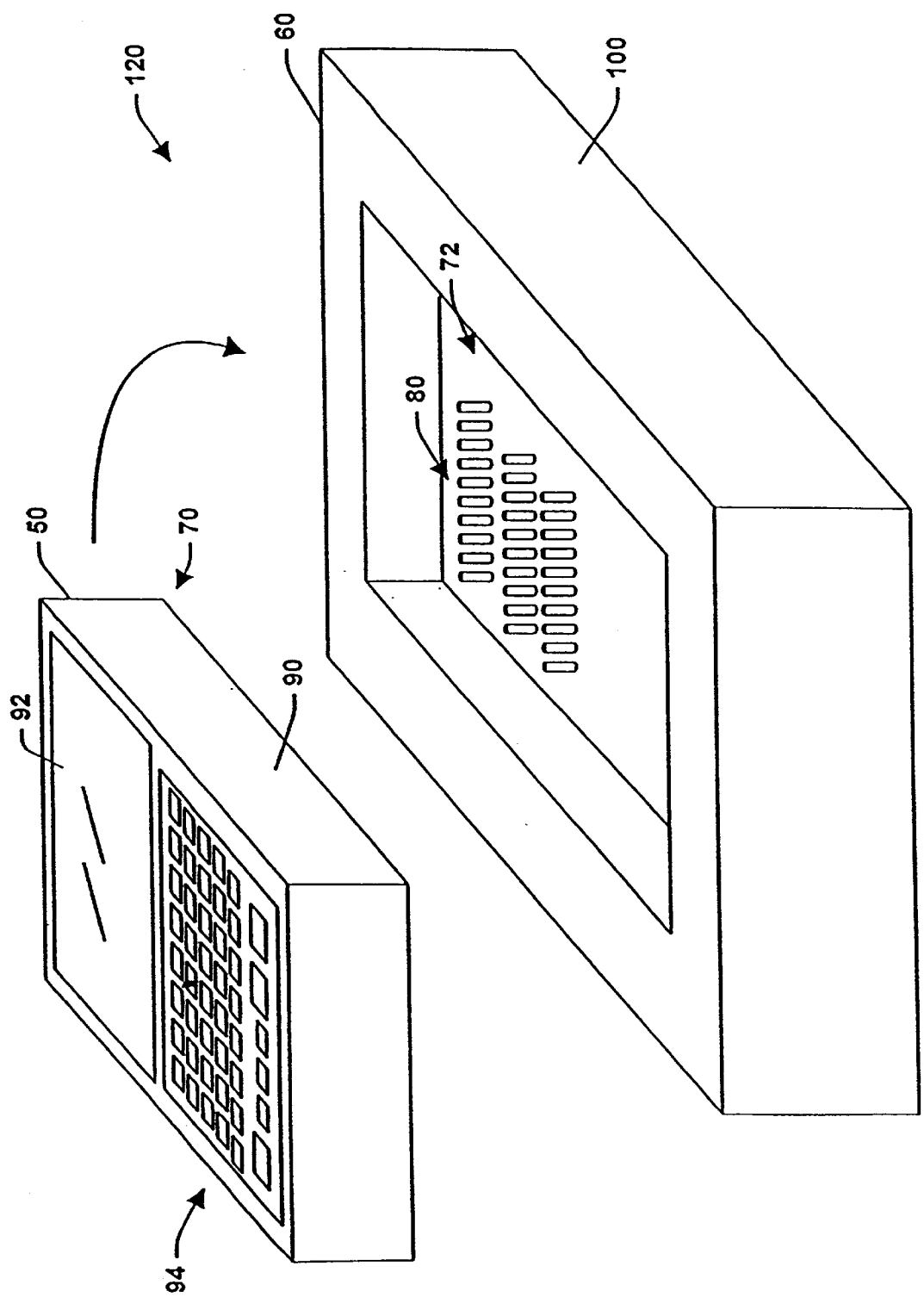
FIG. 2 is a perspective view of a diagnostic module and docking station in accordance with the present invention.

FIG. 2 is a perspective view of the diagnostic module 50 and the docking station 60. As can be seen, the base 70 of the diagnostic module 50 is adapted to fit snuggly into a receiving section 72 of the docking station 60. The diagnostic module 50 is maintained firmly within the receiving section 72 via frictional contact between the outer walls of the base 70 and the inner walls of the receiving section 72. Optionally, spring loaded clips or clamps may be employed to secure the diagnostic module 50—this may be desirable in the case of vertically mounted modules 50. The receiving section 72 includes a plurality of male pin connectors 80 which are designed to mate with corresponding female connectors (not shown) located on the underside of the diagnostic module 50. The pin connectors 80 are operatively coupled to the various sensors disposed within and/or about the machine 30 to collect machine data, and the pin connectors 80 and female connectors (not shown) provide a means for the diagnostic module 50 to operatively couple to the sensors 62 and collect the machine data.

Although the diagnostic module 50 is shown with a rectangular base, and the docking station 60 with a corresponding rectangular receiving section, it is to be appreciated that the diagnostic module 50 and receiving section 72 of the docking station 60 may be of any form and/or shape suitable for carrying out the machinery data collection and analysis system and such is intended to fall within the scope of the hereto appended claims. Furthermore, any suitable docking or coupling system suitable for carrying out the machinery data collection and analysis system may be employed and is intended to fall within the scope of the hereto appended claims.

The diagnostic module 50 includes a housing 90 that is preferably made of metal, high strength plastic, or the like. The housing 90 is an elongated enclosure of a size and including such contours as to conveniently fit into the open palm of a user. In one specific embodiment of the machinery data collection and analysis system, the diagnostic module 50 is fabricated in accordance with a black-box recorder type design as is well known in the art. As such, the diagnostic module 50 would be capable of withstanding damage from catastrophic failure of the machine 30 (e.g., explosion) and/or fire, water, explosion, etc. within the plant employing the machine 30. Such a configuration would provide for safe retention of the machine data which could be employed in possibly determining the cause of the catastrophic machine failure or plant disaster.

The diagnostic module 50 optionally includes a display 92 such as a liquid crystal display (LCD) or the like. The display 14 may be a fine pitch LCD operated as a standard CGA display with a resolution of 640×350 pixels. As is conventional, the display 92 functions to display data or other information relating to ordinary operation of the diagnostic module 50 For example, the display 92 may display general machine operating information such as for example, speed, temperature, torque, voltage, current, related waveforms, bearing health, insulation status, etc. In general, the display 92 provides for a user to quickly visually access and confirm input information relating to the machine 30 and/or operating condition of the diagnostic module 50. Additionally, the display 92 may display a variety of functions that are executable by the diagnostic module 50. As will be discussed in greater detail below, the display 92 is controlled by electronic circuitry within the diagnostic module 50.

The diagnostic module 50 optionally also includes a set of user interface keys 94 for allowing the user to input information and/or operational commands. Although, only a few keys 94 are shown it is to be appreciated that the diagnostic module 50 may include any suitable number of keys for carrying out desired operations. The interface keys 94 may also include a key for manually turning the diagnostic module 50 on and off.

In particular, machines are often employed in harsh environments where heat and exposure to water and other chemicals may be extensive. Thus, the housing of the diagnostic module and housing 100 of the docking station 60 are suitably weatherproofed to protect the diagnostic module 50 and docking station 60. For example, a rubber flange and gasket may be incorporated into the design of the diagnostic module 50 and docking station 60. In addition, the diagnostic module 50 and/or the docking station 60 may be hermetically sealed or potted as required.

FIG. 3 is a schematic illustration of a host computer 110 coupled to a docking station 112 for receiving the diagnostic module 50 after it has completed a predetermined term of data collections. The docking station 112 is similar in design to the docking station 60 and thus detailed discussion related thereto is omitted for sake of brevity. The docking station 112 includes a communications link to the host computer 110 and thus provides for downloaded data from the diagnostic module 50 to the host computer 110. The collected machine raw data and/or processed data is retrieved from the diagnostic module 50 by the host computer 110 via the docking station 112. The host computer 110 may perform further analyses on the raw data and/or processed data in order to facilitate determining a health state of the machine 30 as will be discussed in greater detail below. The docking station 112 also provides for an interface between the host computer 110 and the diagnostic module 50 such the host computer 110 may be employed to reprogram the diagnostic module 50 and/or update the diagnostic module 50 with new motor design information, for example.

Figure 4A:
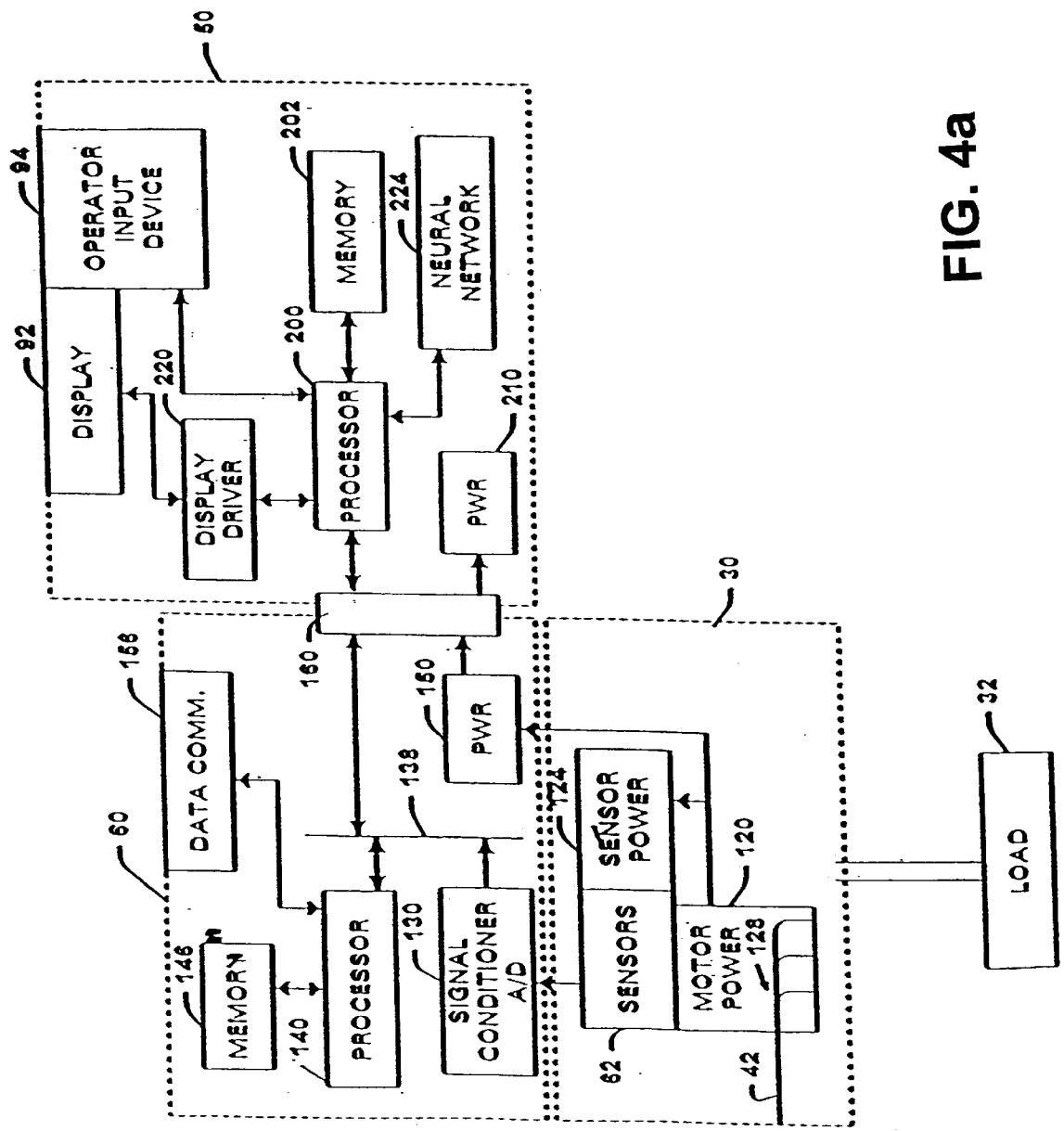
FIG. 4a is a schematic block diagram of a data collection diagnostic system in accordance with one specific aspect of the present invention.

Referring now to FIG. 4a, a schematic representation of the machine 30, docking station 60 and diagnostic module 50 is shown in accordance with one specific embodiment of the machinery data collection and analysis system. As can be seen, the docking station 60 is coupled to the machine 30, and the diagnostic module 50 is coupled to the docking station 60. The motor 30 includes the plurality of sensors 62. Power is provided to the motor 30 via power lines 128. Sensor power 124 is obtained from the motor power lines. It will be appreciated that the motor power is suitably conditioned (e.g., transformed) so as to provide the sensors 62 with appropriate power. The sensors 62 may include: accelerometer(s); temperature sensor(s); thermocouple(s); encoder(s); viscosity sensor(s); voltage sensor(s); current sensor(s); flux sensor(s); optical sensor(s); wear sensor(s); lube sensors; acoustic sensors; brush sensors; ultrasonic sensors, and any other types of sensors suitable for facilitating collecting desired machine related data and carrying out the machinery data collection and analysis system.

The sensors 62 include at least one motor current sensor and in the preferred embodiment three motor current sensors each of which are connected directly to different phase power lead wires (shown as motor power 128) connecting the machine 30 to a source of power. The motor current sensors may be Hall-effect sensors on each power line which generate a signal corresponding to the current flowing through the respective power leads. Alternatively, it will be appreciated that line current may be monitored by separate split core current transformers each clipped on a phase line. As is known, line current is not a direct operating parameter of the motor 30, however, various operating conditions of the motor may be correlated with and derived from line current signatures as is known in the art.

The docking station 60 includes a multi-channel analog to digital (A/D) converter and signal conditioner 130 which is operatively coupled to the sensors 62. The A/D converter 130 provides for converting the analog sensor signals into digital form suitable for processing by a processor.

The signal conditioner includes a demodulator, in this case an RMS-to-DC converter, a device which produces a voltage proportional to the root-mean square (RMS) value (over a preset time interval), of the motor current signal. The demodulated signal is fed through a low pass filter having an upper frequency cutoff below 60 Hz to remove spectra associated with the 60 Hz line frequency and its harmonics. Preferably the demodulation and filtering is implemented via software, however, it is to be appreciated that hardware could be used as well—both techniques are intended to fall within the scope of the machinery data collection and analysis system.

As will be discussed in greater detail below, the conditioned signals are employed by the diagnostic module 50 to facilitate making a health determination of the machine 30. For example, the diagnostic module 50 may extract current signature information from the conditioned current signal obtained from the raw motor current (see e.g., discussion relating to FIGS. 5a, 5b, 6a and 6b). The current signature information may be analyzed across a wide range of frequencies (e.g., fundamental, side band and harmonic ranges) to allow for the diagnostic module 50 to determine the state of the motor 30. However, it should be appreciated that the analysis can be narrowly performed over select frequencies of interest such as critical ball pass frequencies, outer race frequencies, etc., for example.

Similarly, the vibration sensors are employed to collect vibration data relating to the motor 30. Vibration analysis is the established technique for determining the health of mechanical components in rotating machinery such as induction motors. The motor vibration data includes the sum of all the mechanical load changes which refer back to the motor 30. The vibration data also includes effects due to bearing faults and rotor unbalance. Accordingly, the motor vibration information is an indicator of a variety of mechanical and electrical modulations associated with the state of the motor 30. For example, various motor defect situations such as bearing wear, bent shaft, cracks in the various parts of the motor, etc. all manifest themselves through vibrations of the motor 30 (see e.g., discussion relating to FIGS. 5c, 5d, 6c and 6d). To obtain vibration data for machinery analysis, accelerometers as well as associated sampling and filtering techniques are often employed. Larger machines and/or systems may employ proximity sensors to determine vibration.

In using accelerometers, the accelerometers are mounted on the machine being monitored. The location and orientation of the accelerometers is significant to the characteristics of the signal obtained. A vibration generated in one part of the machine is transmitted through the solids separating the source from the accelerometer. The analysis of the vibration signals taken at various times is dependent on the ability to reproduce the precise location and direction of mounting of the accelerometers. Thus, it is preferred that the accelerometers and/or their mounting fixtures be permanently installed on the motor to be monitored. Unlike some conventional machine diagnostic devices, the machinery data collection and analysis system affords for such permanent placement of the vibration sensors integral to or embedded in the machine being monitored.

Since accelerometers sense vibration primarily in one direction (or one plane), multiple sensors are typically necessary to detect the vibrations generated in other directions and in different parts of some equipment. Thus, in order to sense all significant vibration directions, it may be necessary to install multiple-axis sensors. The results obtained are then combined and analyzed to develop the diagnostic information. To obtain good vibration data in order to perform the analysis it is desired to cover at least 5 axes with accelerometers (e.g., a 3-axis accelerometer at the load-end (x, y and z-axes where the z-axis is the axial direction parallel to the shaft) of the machine and a 2-axis accelerometer at the other end (x and y axis)).

Returning back to a discussion of other components of the docking station 60 (FIG. 4a), a bus 138 is provided for coupling various components of the docking station 60 and diagnostic module 50. The A/D converter 130 and a processor 140 of the docking station 60 are coupled to the bus 138. The processor 140 is programmed to control and operate the various components within the docking station 60 in order to carry out the various functions described herein. The processor or CPU 140 may be any of a plurality of processors, such as the p24T, Pentium 50/75, Pentium 60/90, and Pentium 66/100, Pentium PRO and Pentium 2, and other similar and compatible processors. The manner in which the processor 140 can be programmed to carry out the functions relating to the machinery data collection and analysis system will be readily apparent to those having ordinary skill in the art based on the description provided herein.

A memory 146 tied to the processor 140 is also included in the docking station 60 and serves to store program code executed by the processor 140 for carrying out operating functions of the docking station 60 as described herein. The memory 146 includes read only memory (ROM) and random access memory (RAM). The ROM contains among other code the Basic Input-Output System (BIOS) which controls the basic hardware operations of the docking station 60 and pre-stored motor design parameters (e.g., number of slots). The RAM is the main memory into which the operating system and application programs are loaded and temporary storage of raw data and analysis results.

The docking station 60 includes a power supply 150 which derives power from the motor power 120. The docking station 60 also includes a data communication port 156 which is employed to interface the processor 140 with a remote computing device via a local area network (LAN) or wide area network (WAN), for example.

The docking station 60 and diagnostic module 50 interface with each other via an interface 160 which includes the pin connectors 80 (FIG. 2) and corresponding female connectors (not shown). As can be seen, the bus 138 and power supply 150 are connected to the interface 160.

Turning now to the diagnostic module 50, a processor 200 is responsible for controlling the general operation of the diagnostic module 50. The processor 200 is programmed to control and operate the various components within the diagnostics module 50 in order to carry out the various functions described herein. The processor or CPU 200 can be any of a plurality of suitable processors, such as the p24T, Pentium 50/75, Pentium 60/90, and Pentium 66/100, Pentium PRO and Pentium 2, Motorola MC68HC16Z1CFC16 and other similar and compatible processors. The manner in which the processor 200 can be programmed to carry out the functions relating to the machinery data collection and analysis system will be readily apparent to those having ordinary skill in the art based on the description provided herein and thus further discussion related thereto is omitted for sake of brevity.

A memory 202 which is coupled to the processor 200 is also included in the motor diagnostics module 50 and serves to store program code executed by the processor 200 for carrying out operating functions of the motor diagnostics module 50 as described herein. The memory 202 also serves as a storage medium for temporarily storing information such as vibration analysis data, current signature analysis data, motor temperature data, motor voltage data, shaft rotation data, vibration and current spectral tables, and the like which may be eventually downloaded to the host computer 110. The memory 202 may also include machine specific data which is used to facilitate machine diagnosis. For mass data storage, the memory 202 may include a hard disk drive (e.g., 10-Gigabyte hard drive) and/or removable solid state memory (e.g., PCMCIA memory card).

The memory 202 includes read only memory (ROM) and random access memory (RAM). The ROM contains among other code the Basic Input-Output System (BIOS) which controls the basic hardware operations of the diagnostics module 50. The RAM is the main memory into which the operating system and application programs are loaded.

Power is provided to the processor 200 and other components forming the diagnostic module 50 from a power system 210 which may optionally derive power from the docking station 60 when the diagnostic module 50 is docked to the docking station 60. The power system 210 may also include a battery capable of powering the diagnostic module for extended periods of time. It will be appreciated that the power system 210 may also include a charging system for charging the battery when the diagnostic module 50 is docked to the docking station 60.

The diagnostic module 50 optionally includes the display 92 which is coupled to the processor 200 via a display driver circuit 220 as is conventional. The display 92 may be a liquid crystal display (LCD) or the like. In the preferred embodiment, the display 92 is a fine pitch liquid crystal display operated as a standard CGA display with a resolution of 640×350 pixels. The display 92 functions to display data or other information relating to ordinary operation of the motor 30. For example, the display 92 may display a set of discrete motor condition indicia such as, for example, fault indicia, caution indicia, and normal operation indicia which is displayed to the operator and may be transmitted over a network. Additionally, the display 92 may display a variety of functions indicating the operation of the motor 30. The display 92 is capable of displaying both alphanumeric and graphical characters.

The operator input device 94 is also coupled to the processor 200, and as discussed above affords for a user to interact with the diagnostic module 50.

A neural network 224 is coupled to the processor 200 to facilitate data analysis and processing. The use of neural networks for motor diagnostics is well known in the art and thus further discussion relating thereto is omitted for sake of brevity.

Figure 4B:
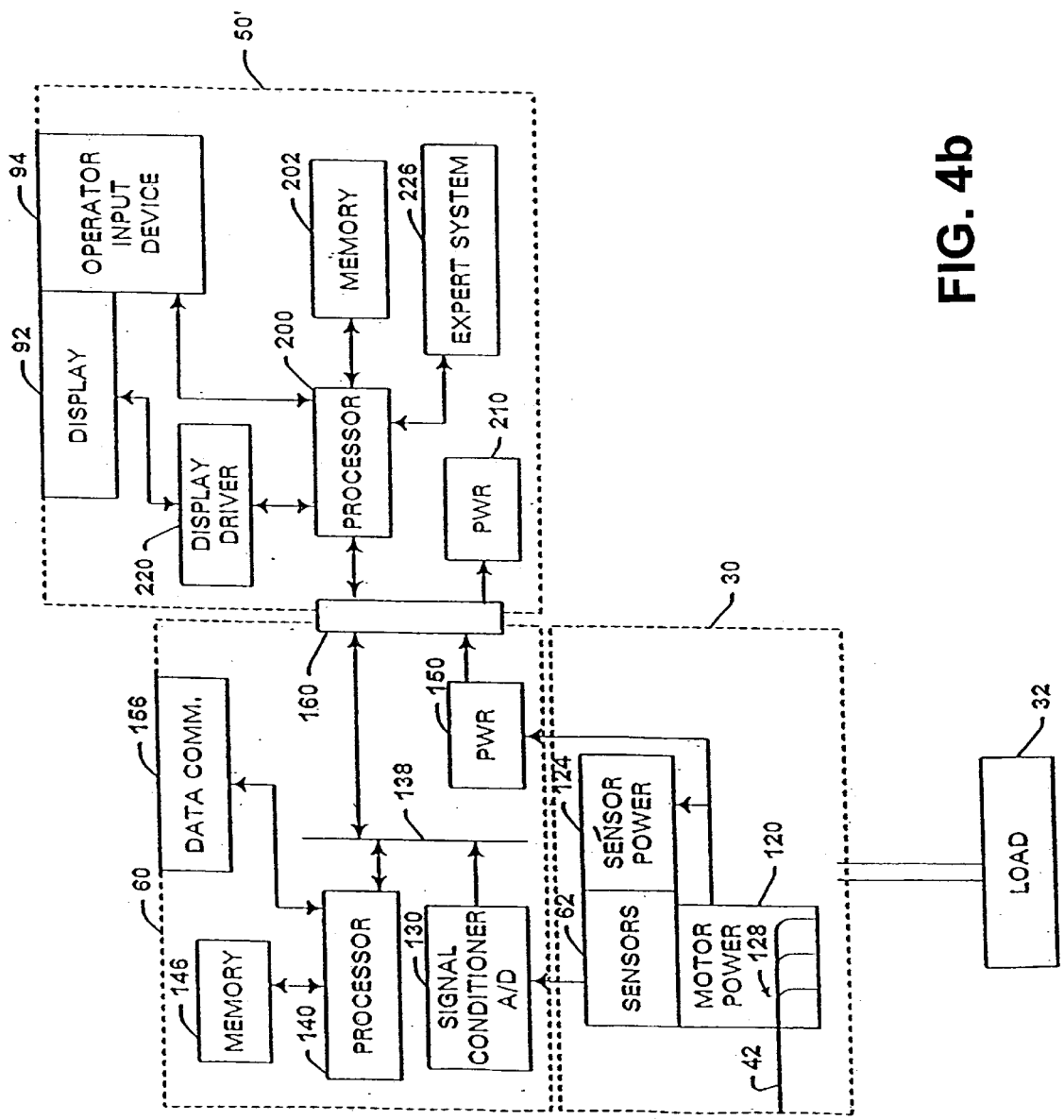
FIG. 4b is a schematic block diagram of a data collection diagnostic system in accordance with one specific aspect of the present invention.

Another embodiment of the diagnostic module 50' employs an expert system 226 in place of a neural network as shown in FIG. 4*b*. The expert system 226 provides for classification based on inference to derive more knowledge about a subject and in turn employ logical reasoning in making a decision regarding the health of the machinery or recommend action.

Expert systems are typically knowledge-based rule-driven systems. The expert system 226 is employed in accordance with the machinery data collection and analysis system by establishing a hardware or software based program which receives input from a knowledge expert as to the nature of the items being sought for classification—in this case motor state. That is, during the training, an expert generates a rule or set of rules for each decision and stores given data into the knowledge base. The expert system 226 will then employ an "inference engine" to establish the health of the system or machine based upon codified expert level knowledge.

Figure 4C:
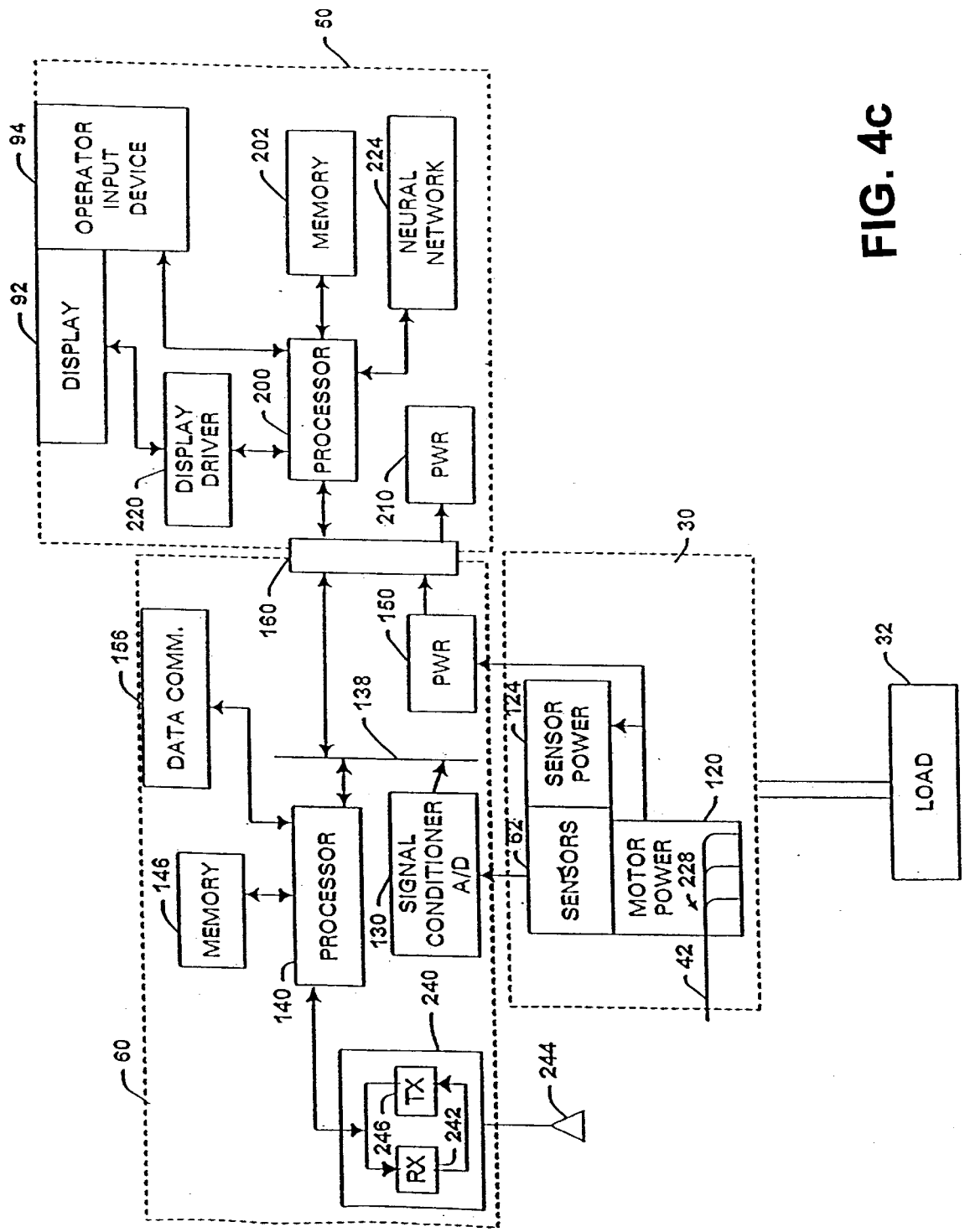
FIG. 4c is a schematic block diagram of a data collection diagnostic system in accordance with one specific aspect of the present invention.

Turning now to FIG. 4*c*, another embodiment of the machinery data collection and analysis system is shown where the docking station 60 includes an RF section 240 connected to the processor 140. The RF section 240 includes an RF receiver 242 which receives RF transmissions from a remote computing device for example via an antenna 244 and demodulates the signal to obtain digital information modulated therein. The RF section 240 also includes an RF transmitter 246 for transmitting information to the remote device for example.

Figure 4D:
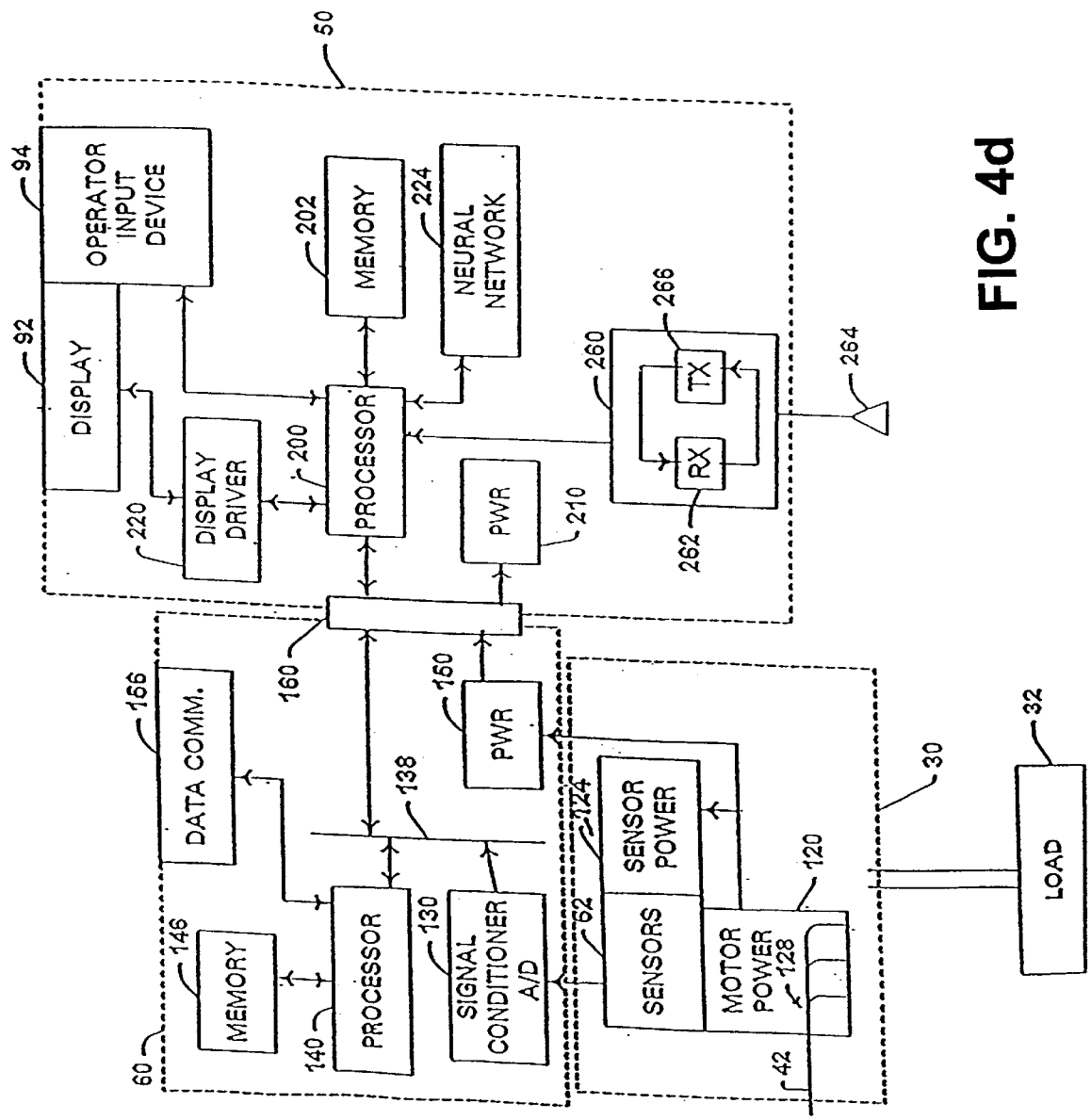
FIG. 4d is a schematic block diagram of a data collection diagnostic system in accordance with one specific aspect of the present invention.

FIG. 4*d* illustrates yet another embodiment of the machinery data collection and analysis system wherein the diagnostic module 50 includes an RF section 260 connected to the processor 200. The RF section 260 includes an RF receiver 262 which receives RF transmissions from a remote device for example via an antenna 264 and demodulates the signal to obtain digital information modulated therein. The RF section 260 also includes an RF transmitter 266 for transmitting information to the remote device for example.

Figure 4E:
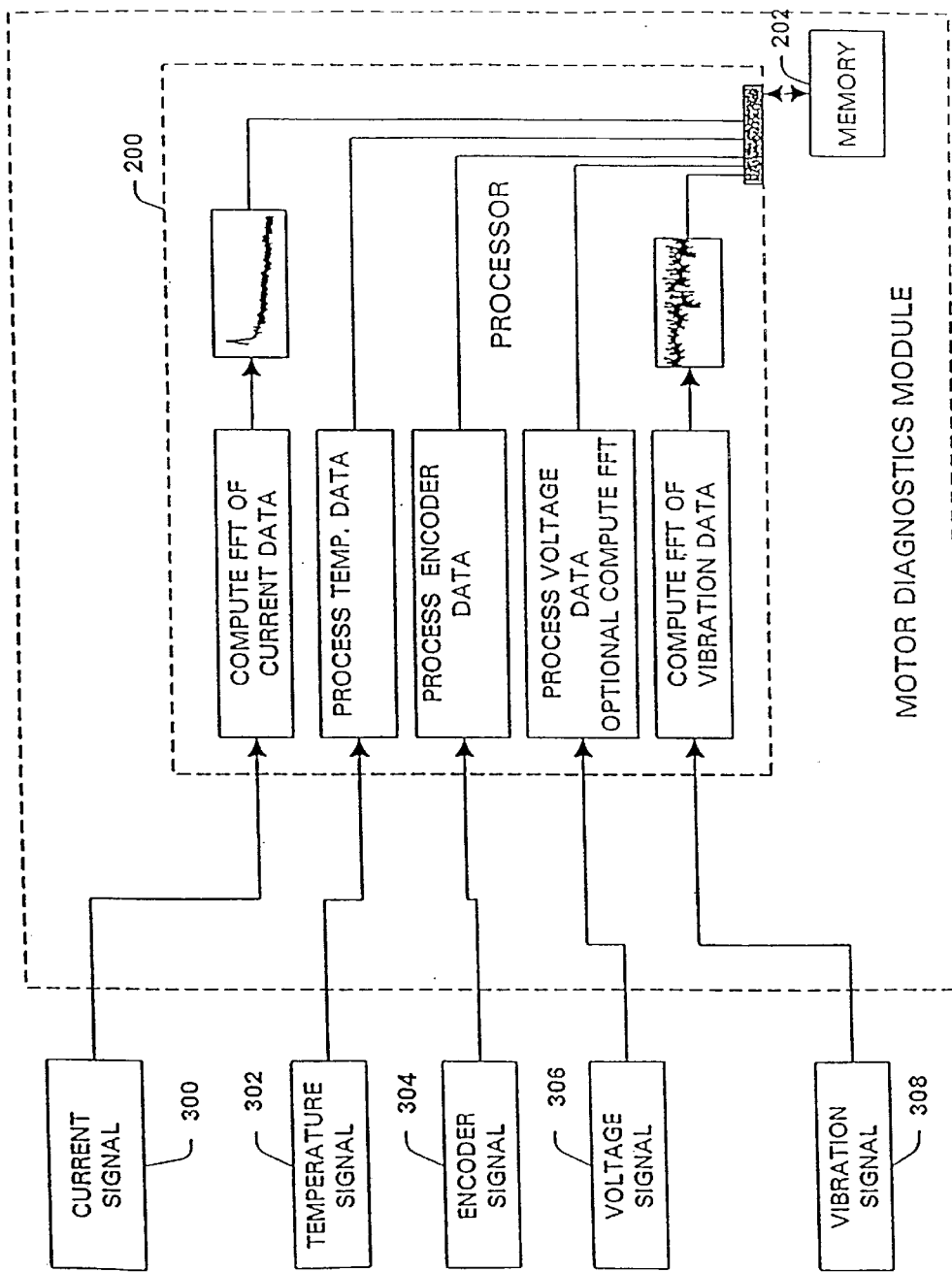
FIG. 4e is a functional block diagram illustrating collection of data relevant to motor health and processing of the data by a dynamoelectric machine diagnostic module in accordance with one specific aspect of the present invention.

Turning now to FIG. 4*e*, a functional block diagram representing the collection of data relevant to the health of the motor 30 and the pre-processing thereof by the diagnostics module 50 is shown. Initially, various sensors are set up to collect motor data. It is to be understood that the present figure is intended to be a representative example of one specific embodiment of the machinery data collection and analysis system. For ease of understanding, this example is limited to preprocessing of five signals from five types of sensors. However, it is to be appreciated that many more types of signals from many other types of sensors may be employed in accordance with the machinery data collection and analysis system and are intended to fall within the scope of the hereto appended claims.

FIG. 4*e* shows five types of signals (current signals, temperature signals, encoder signals, voltage signals, and vibration signals). The current signals 300 are collected by current sensors (not shown) which collect data relating to motor current from the power leads feeding the motor 30. The conditioned and digital current data 300 is provided to the processor 200 which computes fast Fourier transforms (FFr) of the current data for use in current signature analysis.

The temperature signals 302 are provided from temperature sensors (not shown—preferably in the form of thermocouples) which are positioned in suitable areas of the motor 30 to take temperature measurements thereof. For example, a temperature sensor may be positioned to take temperature readings at the front bearings of the motor 30. Another temperature sensor may be located in the stator windings of the motor, and yet another temperature sensor may be positioned to take temperature readings of the rear bearings of the motor. The digital temperature data 302 is provided to the processor 200 for processing.

Encoder data 304 is obtained from an encoder (not shown) suitably positioned about the motor 30 to take readings relating to motor shaft rotation. Like the other data, the encoder data 304 which is conditioned and converted to digital form is processed by the processor 200.

Voltage data 306 is obtained from a voltage sensor (not shown) suitably positioned to obtain voltage data relating to the motor 30. The conditioned, digital voltage data 306 is processed by the processor 200.

As noted above, the motor 30 is also equipped with at least one vibration sensor (not shown) such as an accelerometer for taking sampled vibration data relating to the operation of the motor 30. In the preferred embodiment, a set of vibration sensors is mechanically and rigidly connected to the casing of the motor 30. A three-axis accelerometer may be located at the load end bearing of the motor 30, and a two-axis accelerometer may be located at the other end of the motor 30. However, the machinery data collection and analysis system may be carried out with one, single-axis accelerometer. Preferably, the vibration sensors are laboratory-grade accelerometers such as those manufactured by PCB Piezoelectronics, Inc. Part No. 353B16 and providing 10 mv/g. However, it will be appreciated that any vibration sensor or proximity sensor suitable for carrying out the machinery data collection and analysis system may be employed. The analog signals from the vibration sensors are converted to digital signals by the A/D converter 130 for processing by the processor 200. The accelerometer performs its own signal conditioning and therefore its analog vibration signal is input directly to the A/D 130.

The processor 200 controls the signal sampling and digitizing rate as well as any buffering of the digitized signals 300, 306, and 308 of the sampled data that might be needed. The data collection rate is carried out at for example 26,203 samples per second over a period of 8 seconds. This data collection rate provides sufficient data upon which the processor 200 can generate a comprehensive frequency spectrum of the motor current and motor vibration signals suitable for analysis using commercially available Fast Fourier Transform software such as for example MATLAB by The Math Works. The FFTs of the current signal data, voltage data, and the vibration signal data are discretized over N number of points for ease of processing. In the preferred embodiment, N=2,048, however, it will be appreciated that the FFTs of each signal may be discretized over any suitable number of points. Although, FIG. 4e illustrates FFTs being generated for only the vibration, voltage and current data for ease of understanding, it is to be understood and appreciated that FFTs may be generated for the other data signals (e.g., temperature and encoder) as well.

Figure 5A:
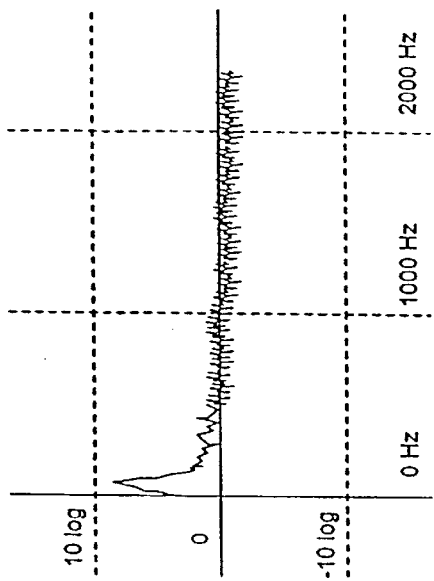
FIG. 5a is a graph of an instantaneous motor current signal for a motor having good bearings in accordance with one specific aspect of the present invention.
Figure 5B:
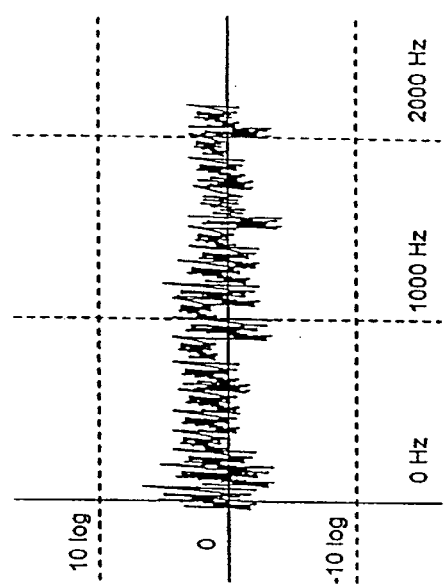
Figure 5C:
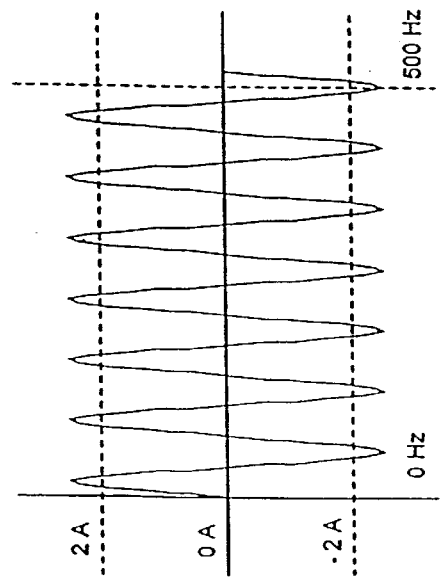
FIG. 5c is a graph of a vibration signal for a motor having good bearings in accordance with one specific aspect of the present invention.
Figure 5D:
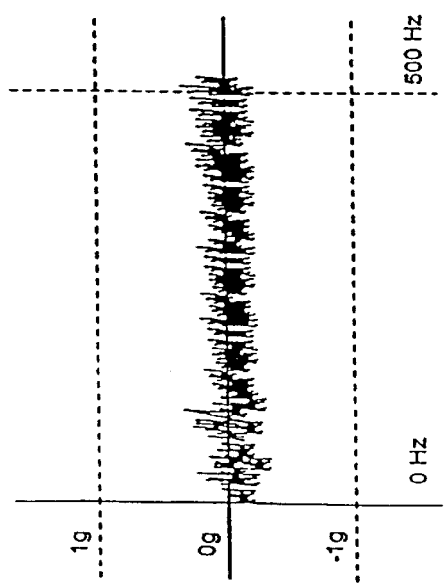
FIG. 5d is a graph of a Fast Fourier Transform signal representative of the vibration signal of FIG. 5c.

Referring briefly to FIGS. 5a–5d and 6a–6d, representative graphs of motor current data, transformed motor current data, motor vibration data and transformed motor vibration data for the motor 30 with good bearings and the motor 30 with bad bearings are shown. The diagnostic module 50 may analyze such data and based on the respective signatures of the current and vibration data make determinations relating to the health of the motor 30 and/or process employing the motor 30. In particular, FIG. 5a is a plot of raw, sampled time domain, current data of a motor 30 with good bearings. FIG. 5b is a corresponding frequency spectrum plot of the raw current data of FIG. 5a. FIG. 5c is a plot of the raw acceleration (i.e., vibration data) taken during the same time frame as the raw current data of FIG. 5a. FIG. 5d is a frequency spectrum plot corresponding to the raw acceleration data of FIG. 5c.

Figure 6A:
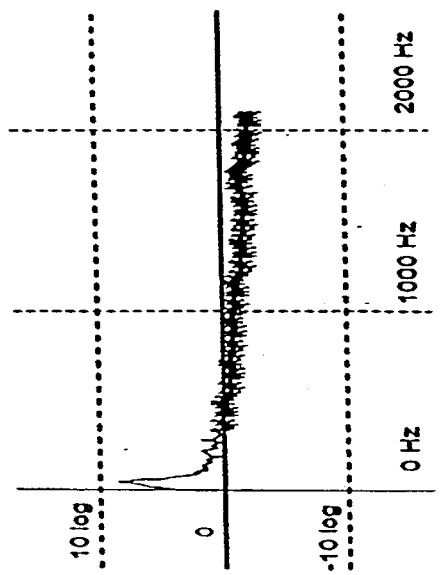
FIG. 6a is a graph of an instantaneous motor current signal for a motor having a bad bearing in accordance with one specific aspect of the present invention.

FIG. 6a is a plot of raw current data of the motor 30 with a bad bearing. In this example, bearing surfaces have been degraded by operating the motor with lubrication contaminated with silicon carbide (SiC) grit.

Figure 6B:
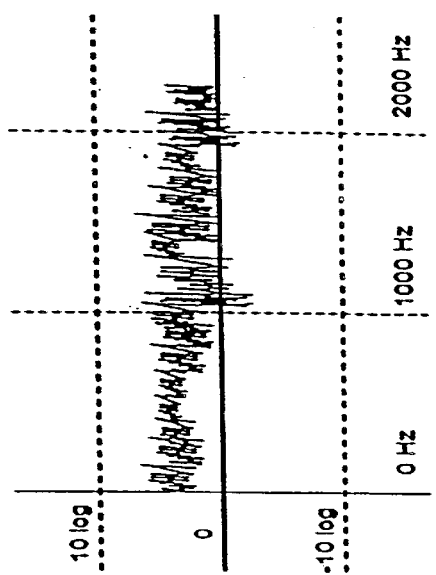
Figure 6C:
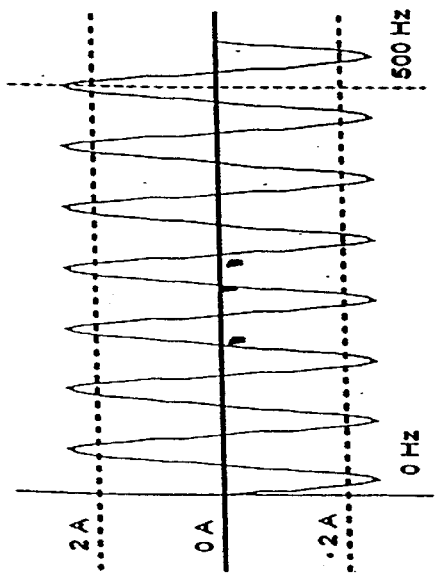
FIG. 6c is a graph of a vibration signal for a motor having a bad bearing in accordance with one specific aspect of the present invention.
Figure 6D:
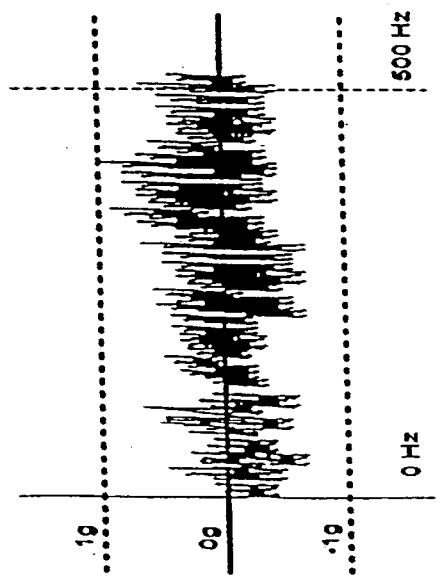
FIG. 6d is a graph of a Fast Fourier Transform signal representative of the vibration signal of FIG. 6c.

FIG. 6b is a corresponding frequency spectrum plot of the raw current data of FIG. 6a. FIG. 6c is a plot of the raw acceleration (i.e., vibration data) taken during the same time frame as the raw current data of FIG. 6a. FIG. 6d is a frequency spectrum plot corresponding to the raw acceleration data of FIG. 6c. A more detailed discussion regarding signature analysis is provided below in connection with FIG. 7.

Returning back to FIG. 4e, once the processor 200 has processed all of the respective motor data, the processed data may be stored in the memory along with the unprocessed data if desired. The processor 200 of the diagnostic module 50 may make a health assessment of the motor 30 if desired. Alternatively, the preprocessed and/or raw sensor data may be delivered to the host computer 110 for analysis. This is achieved by undocking the diagnostic module 50 and redocking it into the docking station 112 coupled to the host computer 110 (see FIG. 3). The host computer 112 may then make determinations as to the health of the motor 30 based on the data received from the diagnostic module 50. Accordingly, motor maintenance can be scheduled to correspond with the state of the motor. Additionally, the processed data can be compiled for trend analysis and forecasting. Since the diagnostic module 50 is integrated with the motor, the data sampling rate can be substantially high thus providing for improved highly accurate and up to date data relating to the current and future health of the motor 30.

It will be appreciated that the memory 146 of the docking station may contain motor specific design information which the processor 200 of the diagnostic module 50 may access to facilitate making a health determination of the motor 30. Alternatively, the memory 202 of the diagnostic module 50 may store design information of all or some of the types of machines it may be collecting data related thereto. The docking station 60 may include some sort of identifying means (e.g., bar code, electrical signal) for identifying to the diagnostic module 50 which type of machine the docking station 60 is coupled to. Thus, the diagnostic module 50 may then access from its memory 202 relevant information corresponding to the particular type of machine.

The diagnostic module 50 may perform many of the tasks (e.g., motor diagnosis, trend analysis, forecasting) that could be performed by the host computer 110.

Turning now to FIG. 7 a table 340 is shown which the processor 200 may access when performing vibration analysis to diagnose the health of the motor 30. The table 340 includes vibration amplitude data ($A_0$ thru $A_z$) over a range of frequencies ($f_0$ thru $f_n$). The table 340 is stored in the memory 202 of the motor diagnostic module 50 so as to be easily accessible by the processor 200 or alternatively stored in the memory (not shown) of the host computer 110 so as to be easily accessible to the processor (not shown) of the host computer 110. The table 340 includes various health states of the motor shown generally at 342 which correspond to vibration amplitudes over the frequency range $f_0$ thru $f_n$. For example, referring to the row identified by reference numeral 346, when the vibration amplitudes are sufficiently close to $A_{234}$ at $f_0$, $A_{27}$ at $f_1$, $A_{478}$ at $f_2$, $A_{24}$ at $f_3$, $A_{127}$ at $f_4$, . . . , $A_Q$ at $f_n$, the table 340 indicates that the motor 30 has a bad bearing. As will be appreciated, the table 340 can store an enormous amount of vibration signatures corresponding to various health states of the motor 30, which the processor 200, for example, can employ to diagnose the health of the motor 30.

The processor 200 or processor of the host computer 110 may utilize various analytical techniques such as those which generally fall under the category of classical vibration analysis which have been proven to detect certain mechanical problems such as, for example, bearing failure, rotor problems, contamination from water or grit, holes in bearings, flat areas on bearings, broken or loose motor mounting, misalignment of motor shaft and load shaft, bent shafts, loose couplings, stator winding problems, fan problems, etc.

Similarly, other tables may be stored in the memory so that the processor can determine the state of the motor 30 with respect to the current signature data, motor temperature data, motor voltage data, motor shaft rotation data, etc.

Although the machinery data collection and analysis system has been described with respect to obtaining Fast Fourier Transforms of the current signals and vibration signals, it should be appreciated that other suitable techniques may be employed. For example, wavelet transforms may be taken of the various sensor data in connection with pattern classification via joint time frequency analysis. Since an original signal C<n> can be recovered from, for example, a polynomial sequence having coefficients C<0>, D<0>, D<1>, ..., D<n-1>, this sequence can be thought of as a transform of the original signal, and is known as a wavelet transform. One advantage to using the wavelet transform is that the total size of the transform C<0>, D<0>, ..., D<n-1> is a compact representation of the original signal and will require considerably less storage than the original signal.

Wavelet transforms have a number of properties that make them attractive for signal processing. For example, if filters are constructed to be sparse, then a filter bank operation can be performed very quickly. Also, for many of the signals encountered in practice, a large percentage of the entries in the wavelet transform are negligible. Wavelet compression methods can therefore approximate the original set of samples in C<n> by storing only the significant coefficients of the wavelet transform.

Wavelets have a variety of applications, for example, wavelets have been used in signal analysis, as discussed in Mallat, "A Theory for Multiresolution Signal Decomposition: The Wavelet Representation," IEEE transactions on Pattern Analysis and Machine Intelligence 11(7):674–693, July 1989. Wavelets have also been used in image processing and numerical analysis, as discussed in DeVore, Jawerth, and Lucier, "Image Compression Through Wavelet Transform Coding," IEEE Transactions on Information Theory 38(2):719–746, March 1992 and Beylkin, Coiftnan and Rokhlin, "Fast Wavelet Transforms and Numerical Algorithm I," Communications on Pure and Applied Mathematics 44:141–183, 1991, respectively. All of these references are hereby incorporated by reference in their entirety.

All that is required for performing a wavelet transform is an appropriate set of analysis and synthesis filters. By using the wavelet transform, a much smaller, compact, training set can be employed, which still enables the machinery data collection and analysis system to reconstruct the original signal information. One particular example of using the compact representation property of wavelets is to generate the wavelet transforms of raw sampled current and raw sampled vibration. Since wavelet coefficients are a compact representation of the original signal, these coefficients can be used directly to perform machinery diagnosis using joint time-frequency domain methods.

This approach also affords for a pseudo frequency domain and time domain analysis of the signal data. Wavelet coefficients thus may provide robust estimates of fractal dimension even in the presence of significant noise. Such an aspect of the machinery data collection and analysis system involves relative simplicity of implementation while affording great flexibility in accommodating a broad range of signal types and noise levels.

It is also to be appreciated that the machinery data collection and analysis system may optionally employ chaos theory. Chaos theory may be a useful tool to facilitate determining system defects and/or rotating machinery problems at early stages. Such techniques, well known in the art, have been shown to be effective indicators of the onset of mechanical instability (e.g., lube breakdown).

Figure 8A:
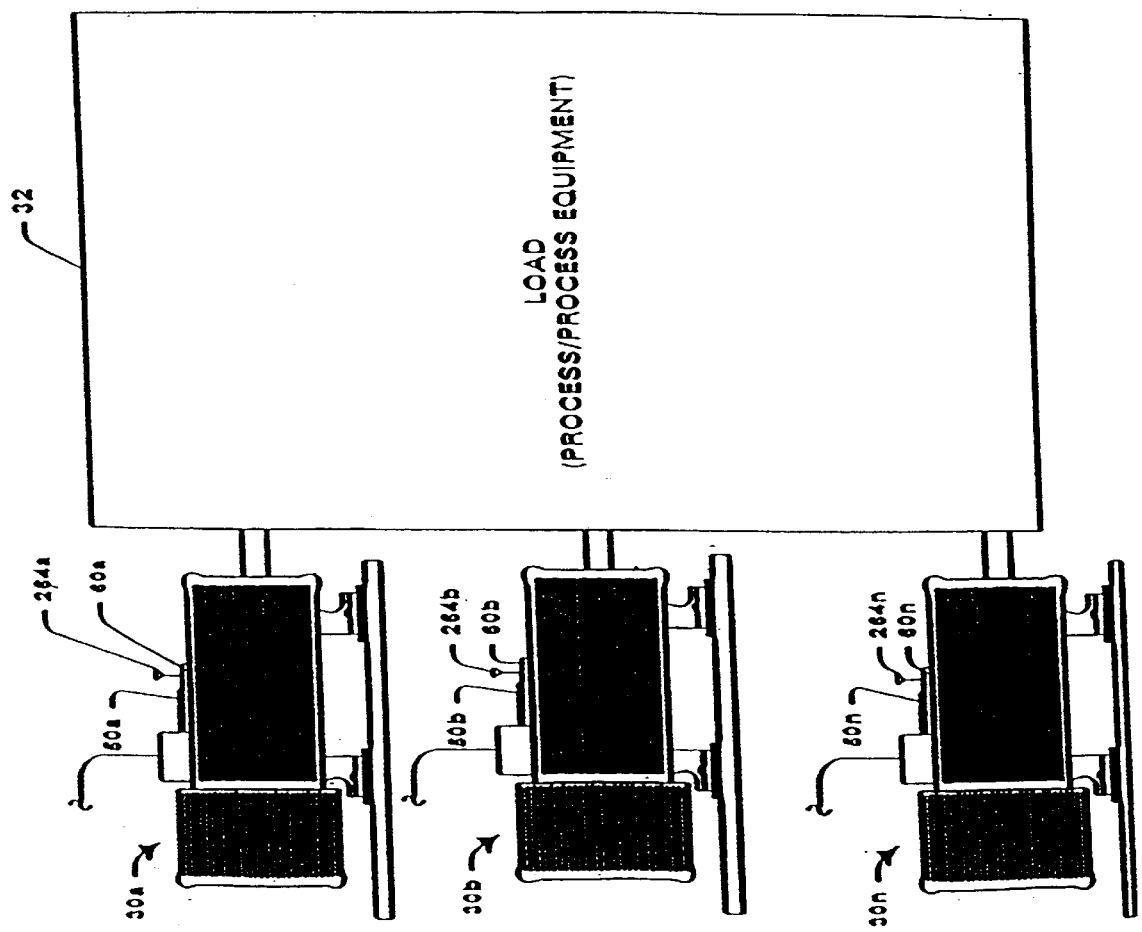
FIG. 8a is a schematic illustration of a load sharing system in accordance with the present invention.

Turning now to FIG. 8*a*, one specific application of the machinery data collection and analysis system is illustrated in connection with load sharing. A plurality of machines 30*a*, 30*b* ... 30*n* (wherein "n" is an integer) are shown sharing a common load 32. Each machine 30*a*, 30*b*, ... 30*n* has coupled thereto a respective docking station 60*a*, 60*b*, ... 60*n*. Coupled to each docking station 60*a*, 60*b*, ... 60*n* respectively are diagnostic modules 50*a*, 50*b*, ... 50*n*. The diagnostic modules 50*a*, 50*b*, ... 50*n* are operatively coupled to each other via a network 370 linking the docking stations 60*a*, 60*b*, ... 60*n* together. The link of the diagnostic modules 50*a*, 50*b*, ... 50*n* may provide for serial data transfer to single modules or multiple addressable modules. Any suitable communications link (e.g., Ethernet, Devicenet) may be employed to carry out the machinery data collection and analysis system. The diagnostic modules 50*a*, 50*b*, ... 50*n* communicate with each other in real time so as to provide for sharing of machine data corresponding to the load sharing between the two machines. It is also to be appreciated that the diagnostic modules 50*a*, 50*b*, ... 50*n* may be coupled to control processors (not shown) of the machines 30*a*, 30*b*, ... 30*n* wherein the diagnostic modules 50*a*, 50*b*, ... 50*n* may provide for coordination of the load sharing as well.

Figure 8B:
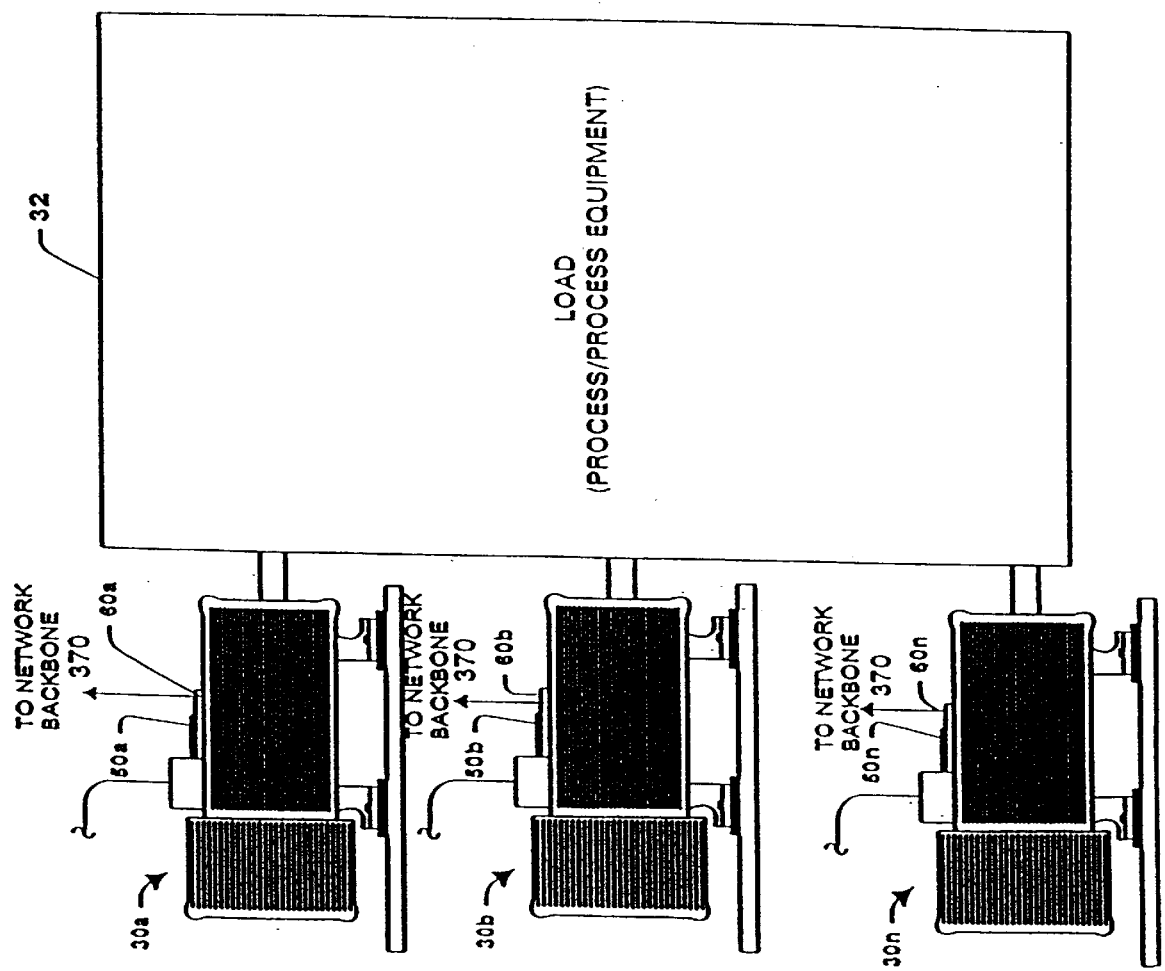
FIG. 8b is a schematic illustration of a load sharing system in accordance with the present invention.

FIG. 8*b* is another embodiment of the machinery data collection and analysis system wherein the modules 50*a*, 50*b*, ... 50*n* communicate wirelessly via antennas 264*a*, 264*b*, ... 264*n* rather than over a network.

Figure 10:
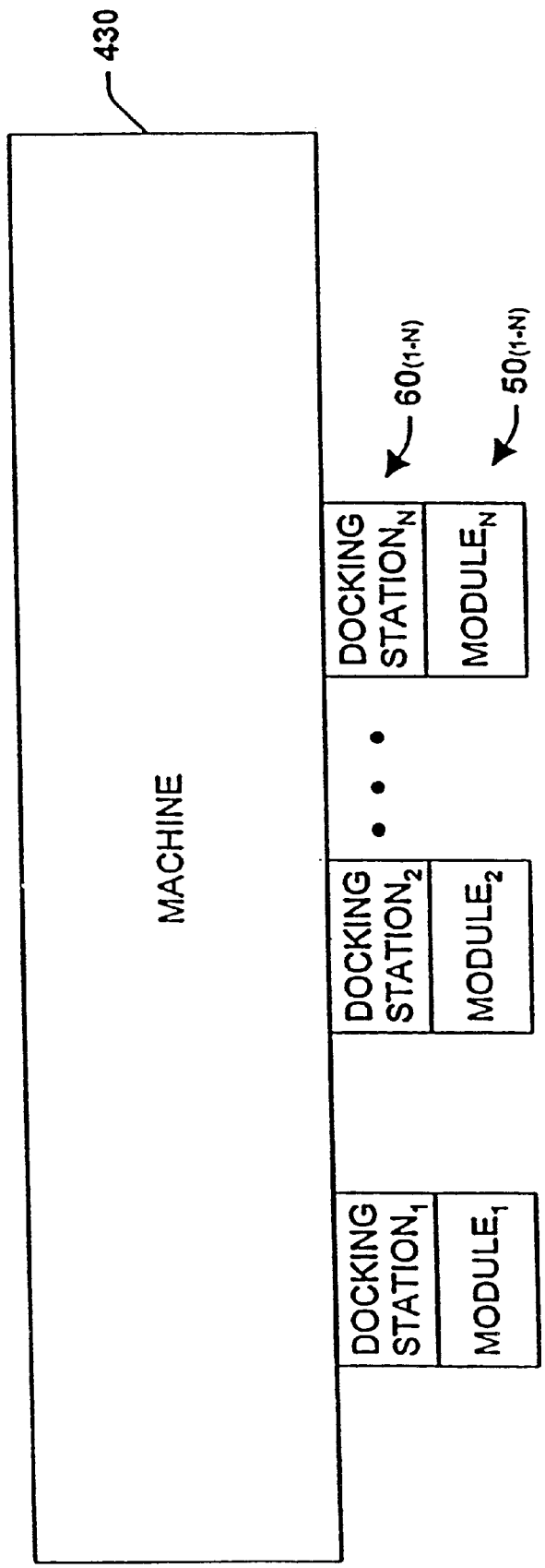
FIG. 10 is a schematic illustration of a system for collecting diagnostic data for a large machine in accordance with the present invention.

FIG. 9 illustrates another embodiment of the machinery data collection and analysis system wherein a plurality of machines$_{1-N}$ are each fitted with respective docking Stations$_{1-N}$, and each docking station$_1$ is adapted to receive a respective diagnostic module$_{1-N}$. Each docking station is coupled to a host computer 400 via a network backbone 402. The host computer 400 may provide for controlling data collection by the respective diagnostic modules. The host computer 400 may also collect the machine data via the network 402. Since the diagnostic modules perform a substantial amount of processing of the raw machine data, network bandwidth requirements are minimized and available network capacity is efficiently utilized. Also, network availability is not critical to maintaining ongoing diagnostics and continuity of stored data. Individual diagnostic modules may collect raw data until the network is again re-established, and a suitable "store & forward" scheme initiated to re-synchronize data collection with the host computer 400. FIG. 10 provides for another embodiment of the machinery data collection and analysis system wherein N number of docking stations 60$_{(1-N)}$ are coupled to a single large machine 430. Each docking station 60 is adapted to couple to a corresponding diagnostic module 50$_{(N-1)}$. Due to large size of some machines, a single docking station and diagnostic module may not be sufficient to collect enough relevant machine data in order to make an accurate health determination of the machine 430. Thus, by using a plurality of docking stations 60$_{(N-1)}$, corresponding sensors can be positioned throughout the machine 430 with mitigating problems associated with introduction of noise because of too long a path between the sensor and docking station 60. This permits docking stations to be standardized for a given complement of sensors and algorithms.

It is also to be appreciated that in such an embodiment, a hierarchy between the respective diagnostic modules 50 may be implemented. For example, all of the diagnostic modules 50 may be operatively in communication with each other (e.g., wirelessly in the manner described above in other embodiments). One of the modules 50 may serve as a master and the other modules 50 as slaves. The master module 50 may provide for controlling and coordinating data collection and processing of the collected data so as to facilitate making an accurate health determination of the machine 430. The use of multiple diagnostic modules on a single machine enables the individual modules to confirm the health and correct operation of all other modules. This facility for self-assessment thus enables the system of modules to be dynamically reconfigured where operating module will assume data storage and processing duties previously performed by failed modules or sensors.

Thus, the machinery data collection and analysis system provides for a system for collecting and processing machine data to facilitate determining a health state of the machine as well as trending performance of the machine.

It is to be appreciated that the machinery data collection and analysis system may be applied to a wide variety of machines (e.g., induction motors, DC motors, DC synchronous motors, AC synchronous motors, and motors driven via inverters, motors driven via SCR soft starts, pumps and gear boxes) and combinations thereof.

What has been described above are preferred embodiments of the machinery data collection and analysis system. It is, of course, not possible to describe every conceivable combination of components or methodologies for purposes of describing the machinery data collection and analysis system, but one of ordinary skill in the art will recognize that many further combinations and permutations of the machinery data collection and analysis system are possible.

B. Data Collection and Analysis System

Figure 11:
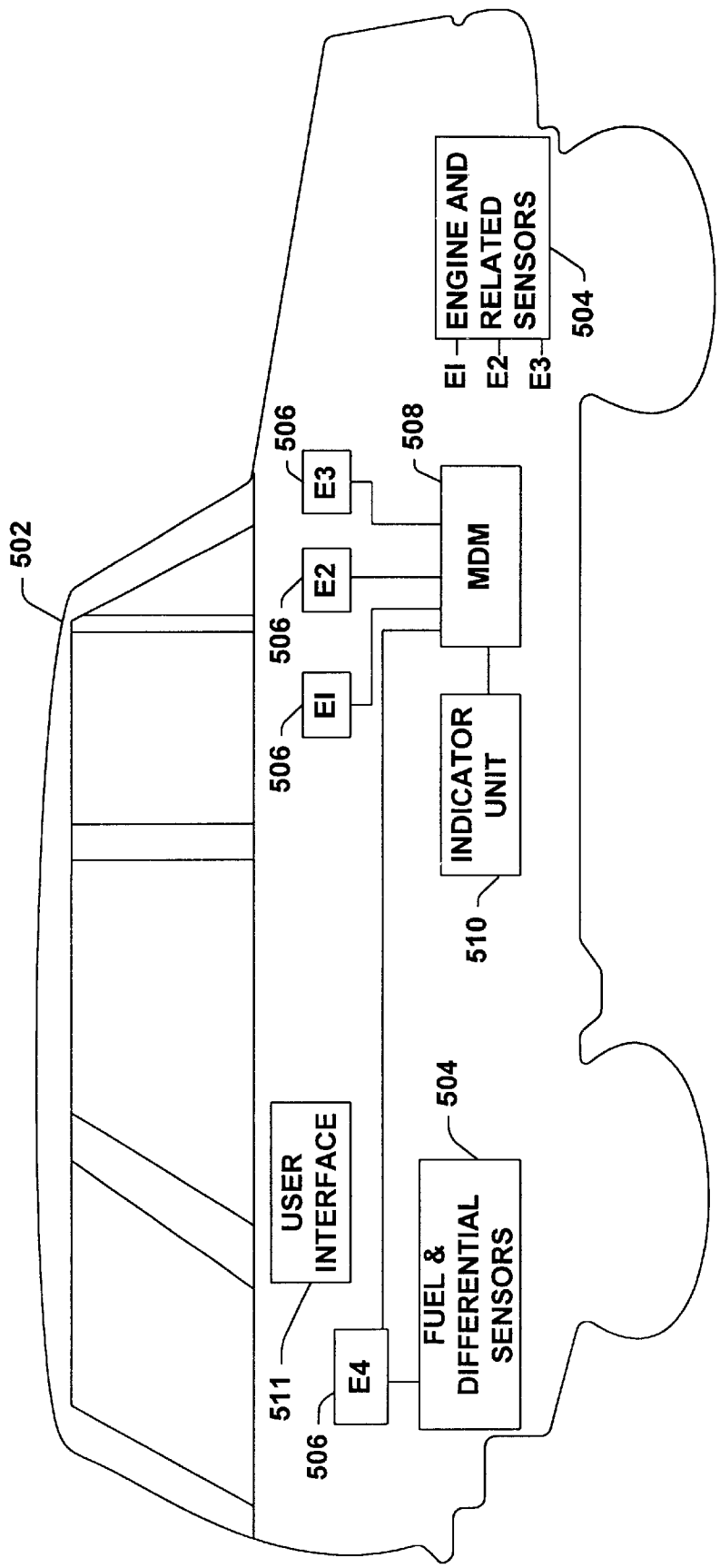
FIG. 11 is a schematic illustration of an on-board vehicle diagnostics system according to a preferred embodiment of the present invention.

Referring now to FIG. 11, a preferred embodiment of an on-board diagnostics/prognostics system 500 is shown installed in a vehicle 502. System 500 includes a plurality of sensors 504, each of sensors 504 being associated with one of a plurality of vehicle subsystems. For instance, vehicle subsystems which may be monitored by system 500 include the engine, the drive train, the suspension, the fuel system, the rear differential, the coolant system, the electrical system, the powertrain system, etc. Preferably, sensors 504 are disposed adjacent to particular vehicle components, and preferably are integrated therewith, to maximize the integrity and sensitivity of the sensors, thus providing reliable health information pertaining to the subsystem.

These integrated sensors 504 collect data pertaining to their respective subsystems, and more particularly, to components (not shown) within the subsystems, and transmit that data continuously during operation of the vehicle to a corresponding one of a plurality of subsystem modules 506. Subsystem modules 506, labeled E1–E4 in FIG. 11, correspond to an engine health module, a drive train health module, a suspension system health module and a rear differential module, each of which is electrically coupled to at least one of sensors 504 to receive data and continuously monitor the health of those subsystems. It is to be understood that the present figure is intended to be a representative example of one specific embodiment of the present invention. However, it is to be appreciated that many more types of signals from many other types of sensors may be employed in accordance with the present invention and are intended to fall within the scope of the hereto appended claims. Notably, subsystem modules 506 preferably store data and have processing capability. Therefore, subsystem modules 506 are capable of continuously updating whether that subsystem is operating in a proper fashion, is degraded in operation, or will fail at a prescribed time in the future.

The outputs of subsystem modules 506 are, in turn, coupled to a master diagnostic module (MDM) 508 that is capable of processing the output from the individual subsystem modules 506 to assess the overall health of the vehicle and determine trends in subsystem and/or overall vehicle performance (described below).

To maximize efficiency and integrity of system health diagnostics and prognostics processes, preferably at least some of the sensors 504 are intelligent sensors for performing data collection and related functions with respect to a variety of vehicle subsystems (although some of the sensors may also be simple low cost transducers). The intelligent sensors preferably include local processing capabilities (filtering, smoothing, variable sampling, and so on), self-diagnostics capabilities, the ability to establish and communicate confidence information pertaining to the accuracy of the sensor data, self-calibrating capabilities, and multi-parameter sensing and sensor fusion features. Especially preferred sensors that each have at least some of these features are now described.

Figure 16:
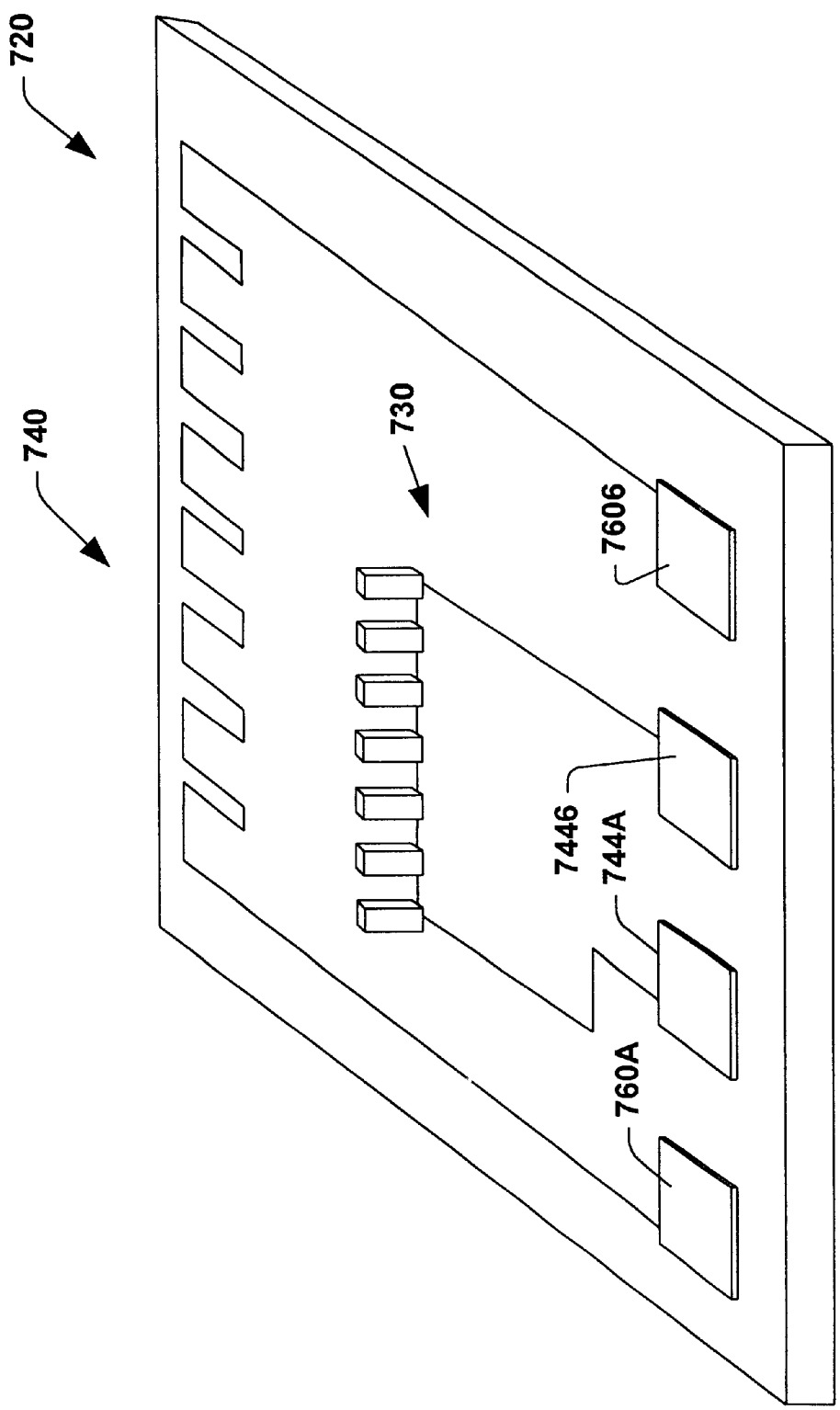
FIGS. 16–18 are preferred sensors that may be used in the vehicle diagnostics system of FIG. 11.

First, the plurality of sensors 504 preferably include a micro-viscosity sensor (FIG. 16) for measuring lubricant viscosity, as disclosed in pending U.S. patent application Ser. No. 09/054,117, assigned to the present assignee, and upon which priority is claimed. The portions of this application that are not re-stated herein are hereby expressly incorporated by reference.

With such a sensor 720, the viscosity of the lubricant can be determined based on the temperature of the lubricant correlated with the power required to oscillate at least one of the sensor elements at a particular frequency. In particular, the micro-viscosity sensor 720 includes at least one finger-like element 730 vertically extending from the surface of a semiconductor base, the at least one finger-like element 730 being oscillated at a desired frequency. The power required to oscillate the at least one finger like element is monitored because the power required is a function of the viscosity of the lubricant. The sensor also includes a temperature detector 740, wherein the thermal conductivity of the temperature detector varies in correspondence with the temperature of the lubricant. A first set of electrical contacts 744a, 744b provides for electrical connection to the at least one finger-like element; and a second set of electrical contacts 760a, 760b provides for electrical connection to the temperature detector. The viscosity of the lubricant is determined based on the temperature of the lubricant correlated with the power required to oscillate the at least one finger like element at a particular frequency.

Figure 17:
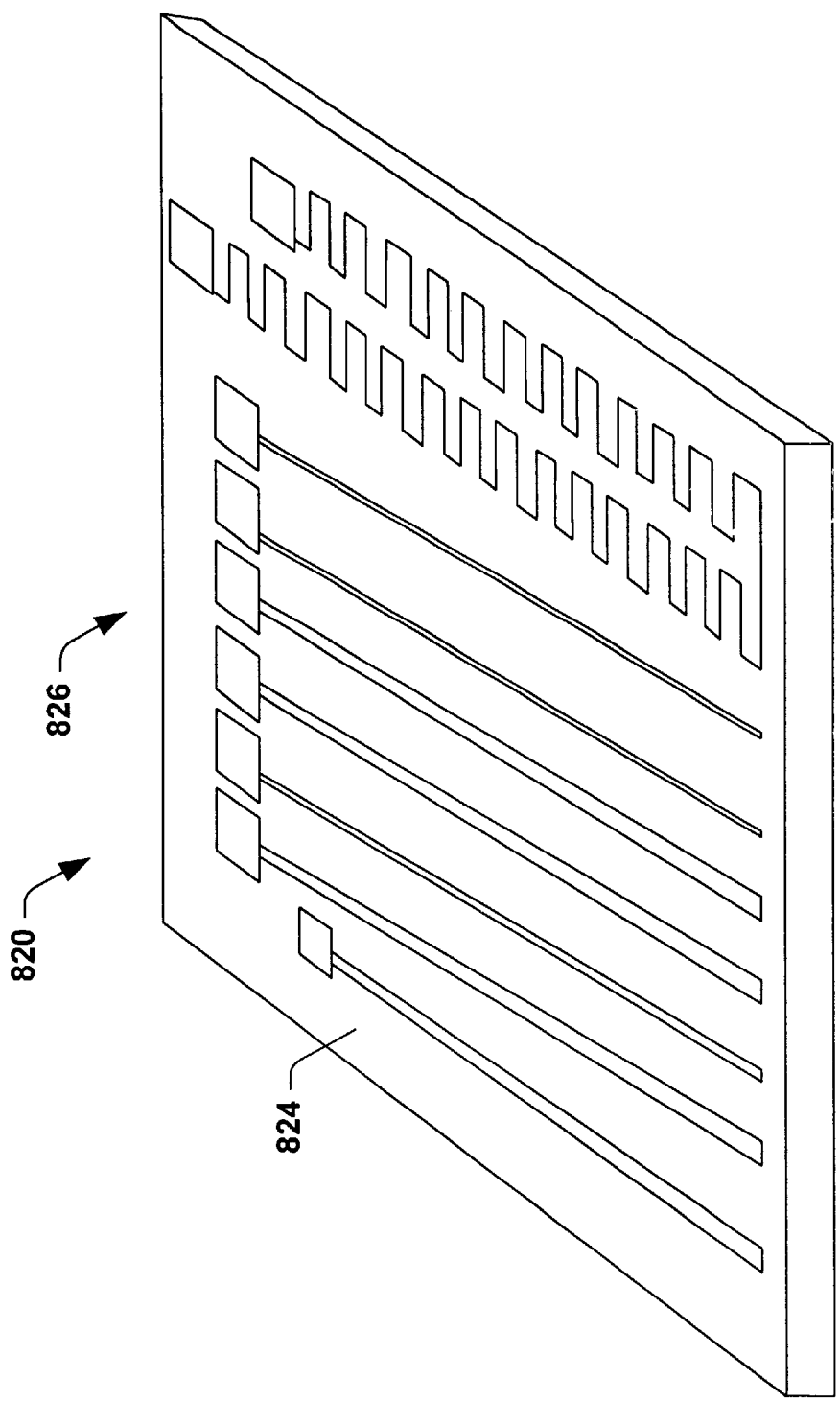

Second, the plurality of sensors 504 preferably also include an integrated multi element lubrication sensor 820 (FIG. 17), as disclosed in pending U.S. patent application Ser. No. 09/300,645, which is a continuation-in-part of the above-mentioned U.S. patent application Ser. No. 09/054,117, and which is also assigned to the present assignee, and which upon priority is also claimed. The portions of this application that are not re-stated herein are hereby expressly incorporated by reference.

The integrated multi-element fluid sensor system 820 is usable to determine the health state of a fluid and includes at least two sensors 826 for collecting data relating to a particular parameter (e.g., pH, temperature, conductivity, chemistry, viscosity) of the fluid. The at least two sensors 826 may be integrated onto a semiconductor base 824 so as to provide for a microsensor for in situ monitoring of the fluid. The system also includes a data fusion processor operatively coupled to the at least two sensors. The data fusion processor processes the fluid data to at least compensate for information fragmentation attributed to using the at least two sensors. The data fusion processor may condense the data, combine the data, evaluate the data, and interpret the data.

Figure 18:
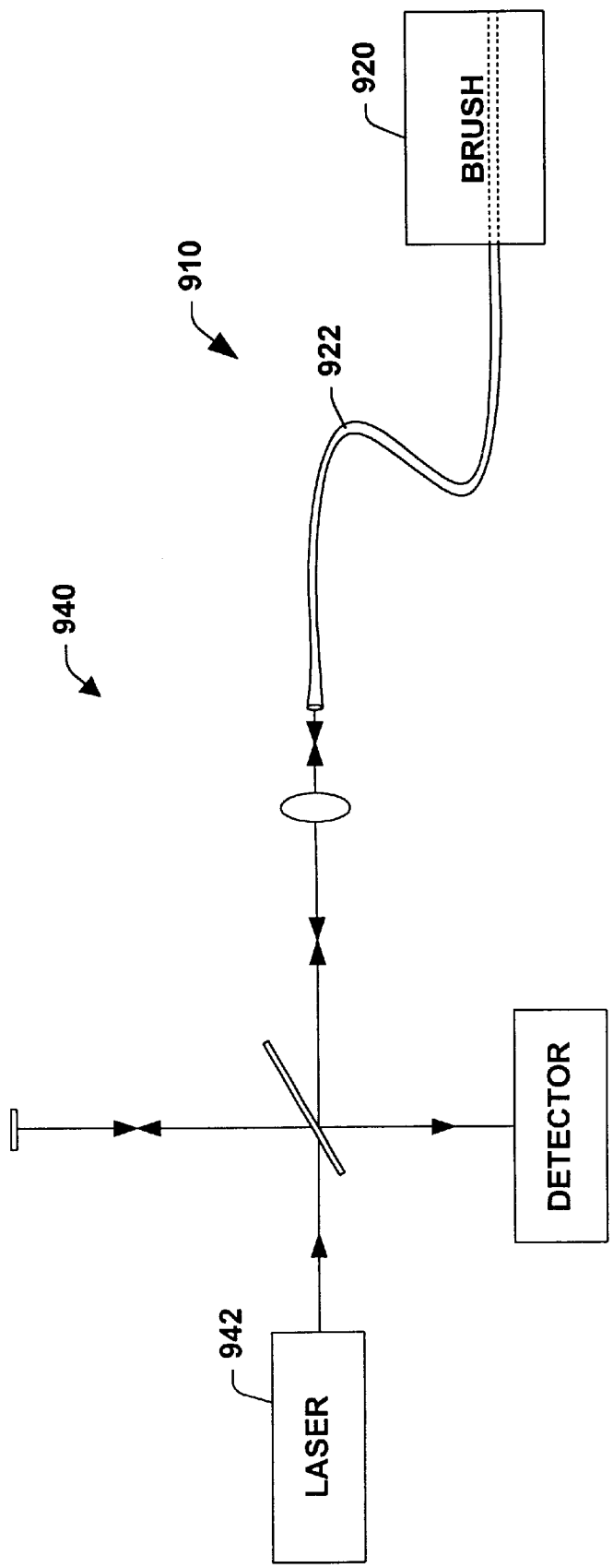

Third, the plurality of sensors 504 preferably also include a sensor 910 (FIG. 18) for determining the wear of an article, as disclosed in pending U.S. patent application Ser. No. 09/253,785, assigned to the present assignee, and which upon priority is also claimed. The portions of this application that are not re-stated herein are hereby expressly incorporated by reference.

The wear sensor 910 includes an optical fiber 922 for transmitting light from a light source 942. The optical fiber is embedded in the article 920, and operatively coupled to an interferometric system 940. The interferometric system 940 is operatively coupled to a processor. The interferometric system 940 provides the processor with information relating to wear of the optical fiber 922, and the processor determines wear of the article 920, rate of wear, and remaining useful life of the article 920 based on the information relating to wear of the optical fiber 922. The wear sensor 910 is well suited for monitoring the health status of vehicle subsystems, and in particular as a brake wear sensor that may be integrated into each wheel for real-time measurement of brake life remaining and the rate of brake pad wear so as to facilitate predicting a replacement interval.

The plurality of sensors 504 also preferably include a sensor that utilizes a multi element lubrication sensor packaging system as disclosed in U.S. patent application Ser. No. 09/257,680, filed Feb. 25, 1999, pending, assigned to the present assignee, and which upon priority is also claimed. The portions of this application that are not re-stated herein are hereby expressly incorporated by reference.

These and other intelligent sensors can be implemented as, for example, engine oil sensors, radiator sensors, transmission fluid sensors, fuel sensors, etc. to gather data pertaining to the health of particular components within subsystems 506 associated with those sensors 504. Each of the previously identified intelligent sensors may be integrated with CAN-based networks already existing on many of today's vehicles.

Alternative sensors 504 may also be utilized. For example, a photoelastic neural-net torque sensor such as that disclosed in U.S. Pat. No. 5,723,794, the disclosure of which is hereby expressly incorporated by reference may be utilized. Such a torque sensor is useful for monitoring drivetrain components and vehicle steering. Notably, subsystems such as the drive train may be dynamically coupled to other subsystems such as the engine, thus the torque sensor may also function as a useful source of overall vehicle health information.

Still referring to FIG. 11, an indicator unit 510 may be provided within vehicle 502 to convey alert information from either subsystem modules 506 or master diagnostic module 508 to the user as these modules continuously provide real-time health assessment of the subsystems, alone and in combination, of the vehicle. Indicator unit 510 can be an audio alarm, a display or any other suitable indicating unit for conveying alert information to the user. In addition, a user interface may be included for allowing the user to input vehicle operational parameters. For example, the user can indicate that the vehicle will be traveling at particular speeds, over particular topography or for a set distance. This input can affect the vehicle health assessment, failure prediction and maintenance schedule, as discussed below.

Figure 12:
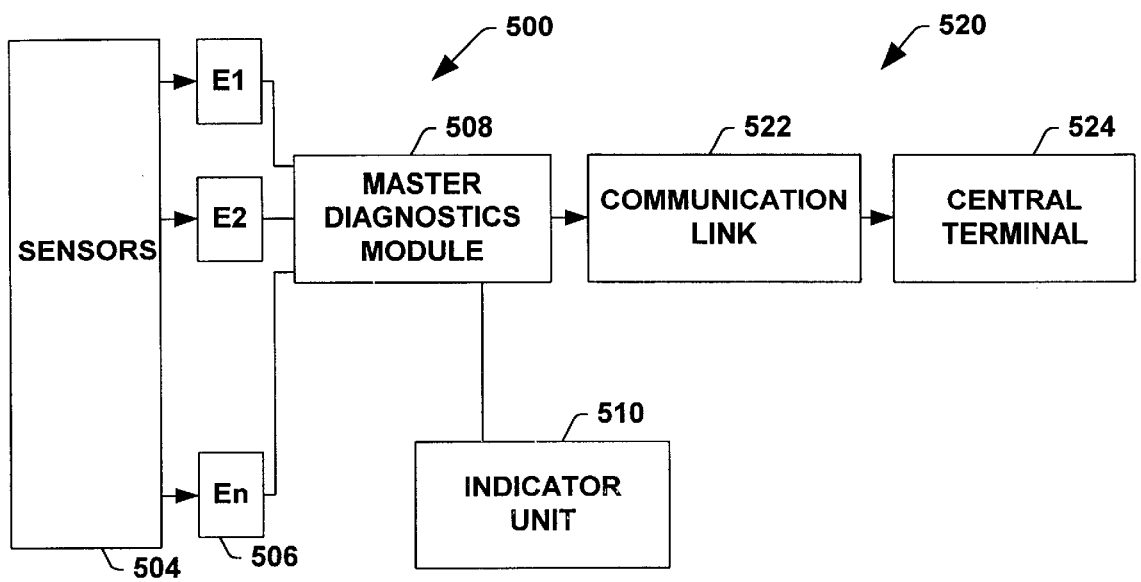
FIG. 12 is a block diagram of the vehicle diagnostics system of FIG. 11 shown coupled to a central terminal.

Referring next to FIG. 12, a preferred embodiment 520 of the present invention combines on-board vehicle diagnostics system 500 with a central terminal 524 via a communication link 522. Again, sensors 504 are mounted on-board, for example, vehicle 502 to collect data relating to vehicle subsystems and generate data signals for transmission to a plurality of subsystem modules 506 (E1, E2 . . . , $E_n$). Once processing of the data signals gathered by sensors 504 is at least generally complete (i.e., once subsystem modules 506 and master diagnostics module 508 perform diagnostics and prognostics analysis), the memory contents pertaining to subsystem health of master diagnostics module 508 are transmitted to central terminal 524 for storage of information related to that vehicle and/or for further processing of the information. For instance, master diagnostics module 508 may operate as a health assessment device while central terminal 524 operates as a trending and maintenance scheduling unit. For this purpose, central terminal 524 typically uses a host computer (not shown) for processing the information received from master diagnostics module 508.

According to one embodiment, communication link 522 is a docking station (not shown) adapted to receive master diagnostics module 508. Notably, while subsystem modules 506 preferably are permanently mounted within the vehicle, while master diagnostics module 508 is configured to be removably received by a docking station (not shown) mounted within vehicle 502. As such, master diagnostics module 508 may be readily removed for conducting further processing of the information contained therein. To minimize vehicle downtime while in for service, a substitute master diagnostics module 508 can be exchanged therefor. In particular, in this case, central terminal 524 is preferably stocked with substitute swappable master diagnostics modules 508.

Alternatively, the communication link 522 may be a wireless link. For example, master diagnostics module 508 can be equipped with an antenna (not shown) to allow radio communication with a radio receiver (not shown) housed at central terminal 524. Of course, other wireless technologies may be utilized including cellular, radio, paging networks, etc. Overall, wireless links permit real-time transfer of information relating to the health of the vehicle such that, for example, a dispatcher can intelligently and reliably determine when that vehicle will require maintenance (and for what system component) while the vehicle is in route.

Figure 13:
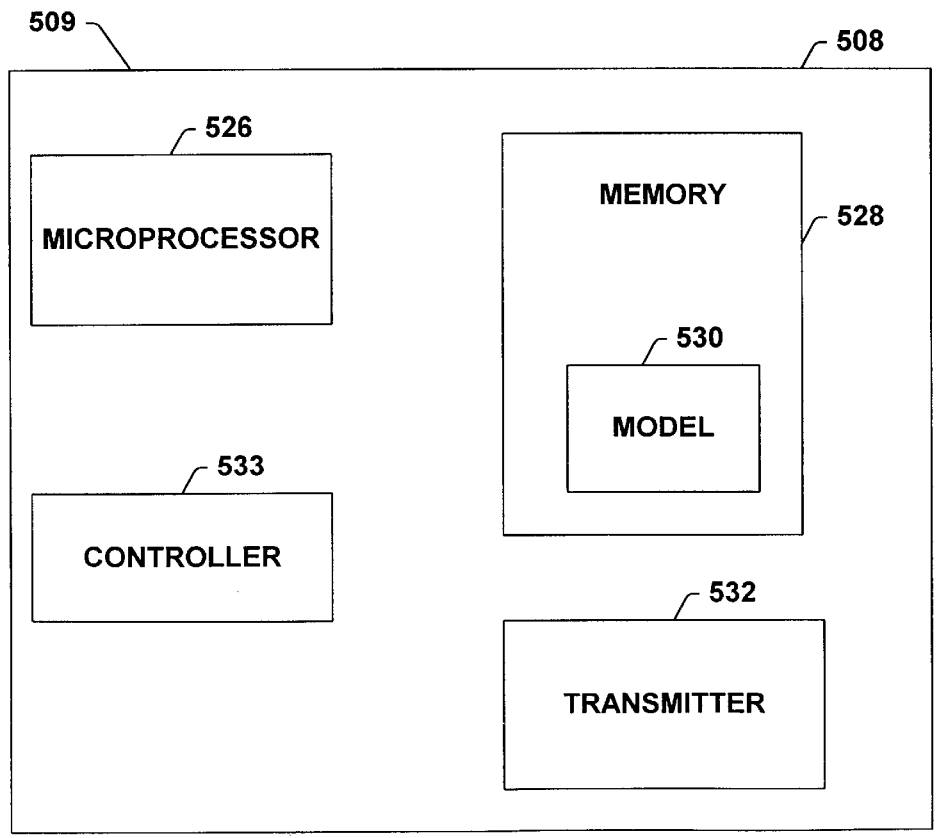
FIG. 13 is a block diagram of the subsystem module and the master diagnostics module shown in FIGS. 11 and 12.

Turning to FIG. 13, a more detailed block diagram of a preferred master diagnostics module 508 (and at least one embodiment of subsystem modules 506) includes an input port 509 for receiving subsystem health assessment signals from subsystem modules 506. Master diagnostics module 508 also includes a microprocessor 526 for processing the input to perform diagnostics and prognostics analysis. Processor 526 is responsible for controlling the general operation of module 508 (and, preferably, modules 506). Processor 526 is programmed to control and operate the various components within the diagnostics module 508 (or 506) in order to carry out the various functions described herein. As in the machine embodiment, processor 526 can be any of a plurality of suitable processors, such as the p24T, Pentium 50/75, Pentium 60/90, and Pentium 66/100, Pentium PRO and Pentium 2, Motorola MC68HC16Z1CFC16 and other similar and compatible processors.

To store health assessment information, master diagnostics module 508 includes a memory 528 that is capable of storing substantial amounts of data, thus facilitating continuous real-time diagnostics and prognostics capabilities. Memory 528 also preferably includes an embedded model 530 that can be utilized by processor 526 in health assessment and trend analysis.

More particularly, utilizing a model 530 facilitates accurate diagnostics and prognostics analysis, thus allowing vehicle diagnostic system 500 to efficiently determine when maintenance is or will be required. Each of the operating environments, component specifications, user requirements, component and subsystem arrangement and other related information are utilized in the design of the models 530. The models 530 are formulated so as to evaluate the sensed data to render accurate determinations as to when particular subsystems, and components associated therewith, will require maintenance based on data generated by all of the subsystems, and the health assessment information produced by individual subsystem modules 506.

The models 530 assess overall health of the vehicle such that, for instance, system 500 is not only able to determine when a sensed vibration is due to an out-of-balance tire (rather than, for example, a bad bearing problem), but also to determine that, due to the vibration, irreparable harm is being done to a particular subsystem independent of the subsystem 506 associated with the component therein. Further, the system is able to determine that, even though the sensed vibration may not pose an immediate threat of harm or legitimate maintenance concern for the tire, the vibration resulting from that tire imbalance has a significant impact on another subsystem or component thereof. By analyzing the particular type of vibration sensed, in conjunction with the architecture of model 530, master diagnostics module 508 can make a highly accurate and reliable health assessment. Most notably, the model provides information regarding how subsystem components degrade and wear over time such that master diagnostics module 508 can properly assess, when particular subsystems, or components thereof, require maintenance or when in the future they will require maintenance.

The model preferably includes at least four software modules. The first module establishes the accuracy and consistency of the input from each subsystem 506. The second module provides a simulation of the subsystems and overall vehicle operation. Both quantitative and qualitative (e.g., causal network) models are preferably employed in the second module. The third module establishes future driving scenarios and likely stresses the vehicle will encounter. The fourth module uses conventional statistical estimation and time series analysis methods to perform time-based forecasting of the wear and degradation of various system components.

Note that, with continued reference to FIG. 13, master diagnostics module 508 may also include a transmitter 532 for conveying health assessment information to central terminal 524 (FIG. 12). For instance, transmitter 532 can be a radio transmitter, cellular datalink, a paging transmitter, or any other suitable wireless transmitter. Moreover, module 508 may include a controller 533 that is capable of generating subsystem control signals in response to module health assessment processing (described below). Briefly, based upon the health of a particular subsystem (or component thereof), controller 533 may generate and transmit a control signal to either that subsystem 506 or a related subsystem to alter its operation, and to lessen the effects of any fault-producing stimuli.

Figure 14A:
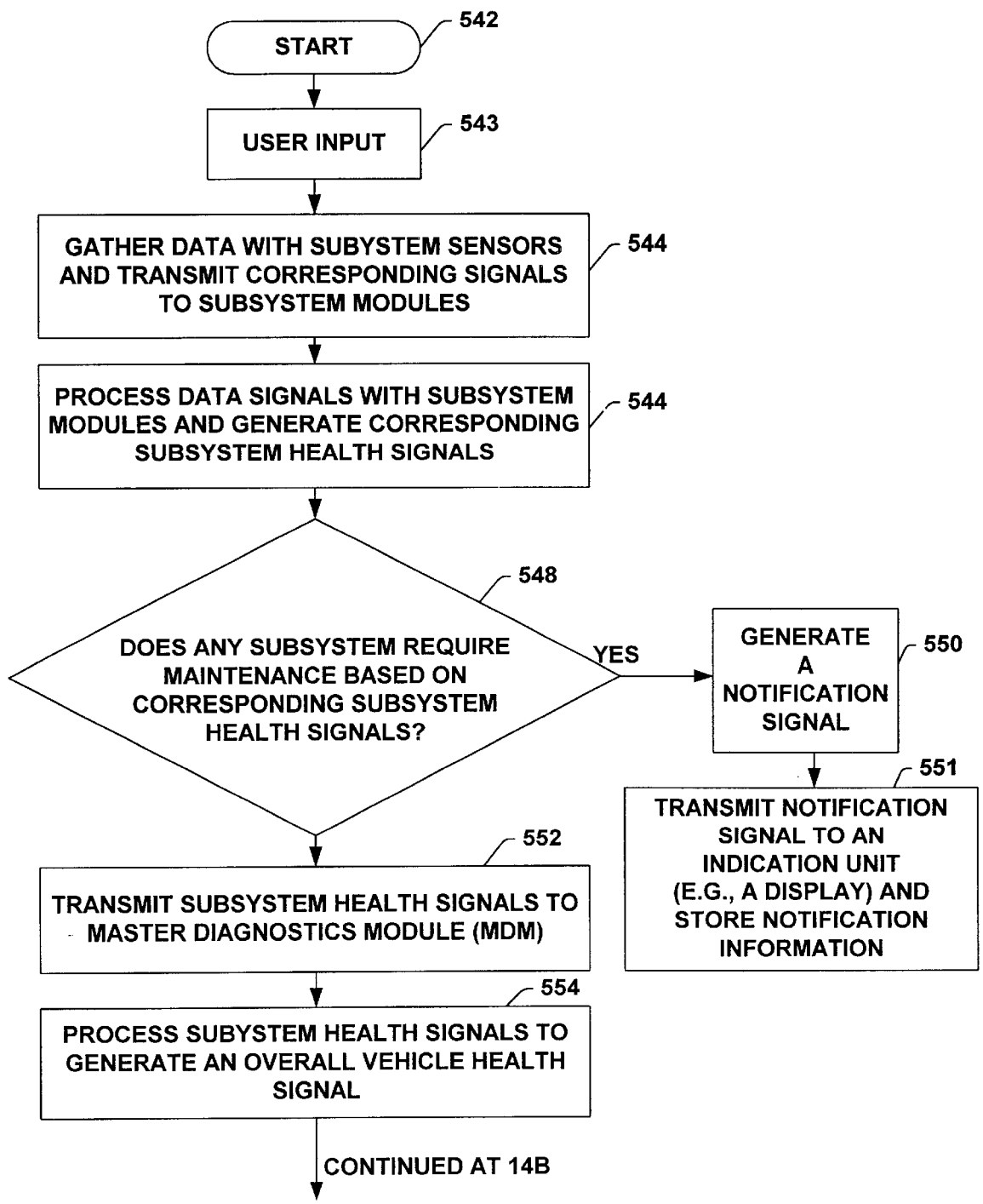
FIGS. 14a–b is a flow chart showing the general operation of the vehicle diagnostics system of FIG. 12.
Figure 14B:
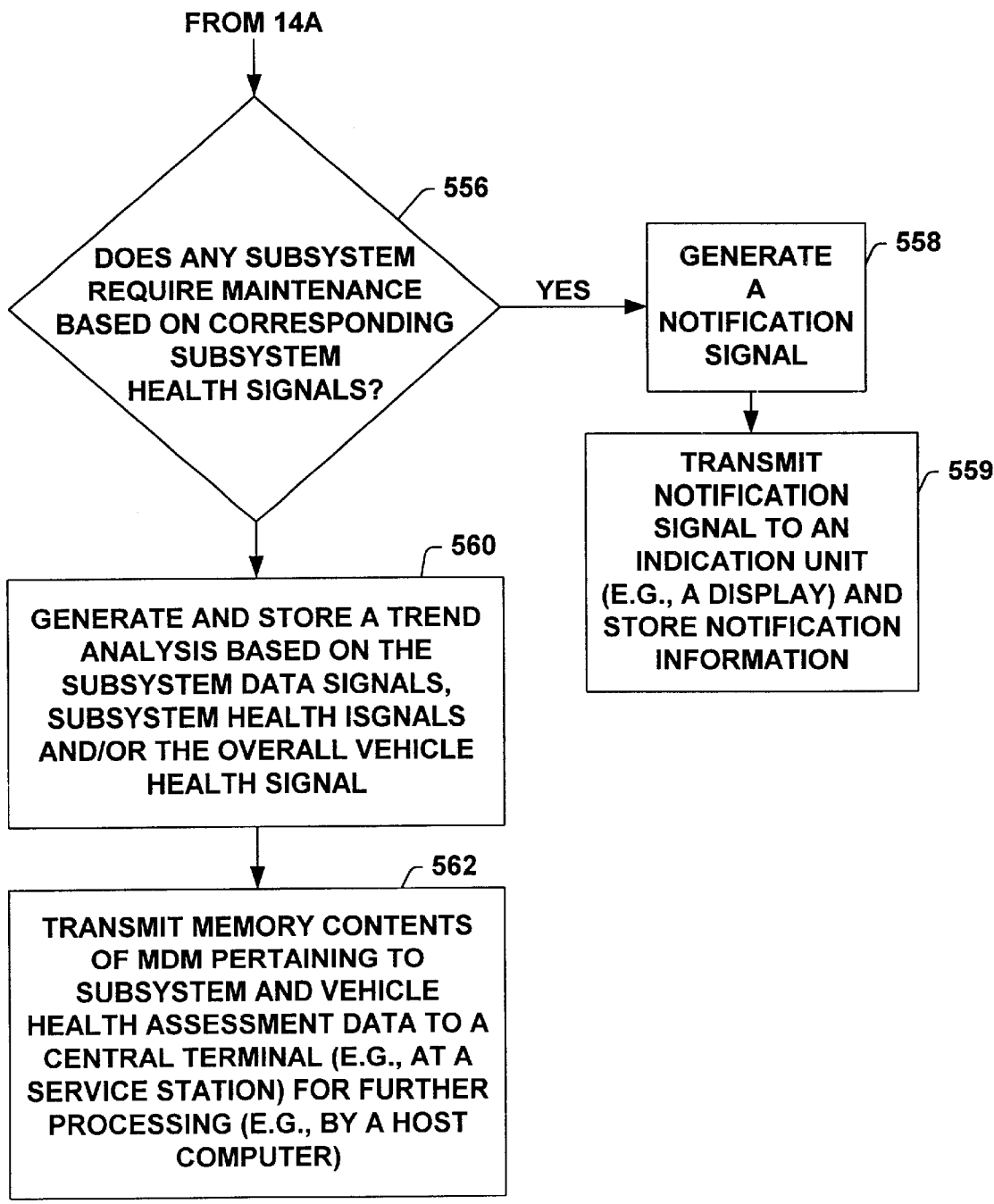

Turning to FIG. 14a and 14b, the general operation of system 500 is indicated by system program 540. After start up and initialization at Step 542, program 540 executes Step 543 to receive data from the user interface which, as described previously, may comprise particular operating parameters such as average expected speed, unique trailer or load information, expected trip distance, etc. These user input parameters will be factored in, as well as any system model (described below) when generating subsystem and vehicle health assessments. Next, at Step 544, system 500 operates to gather data using subsystem sensors 504, and thereafter generate and transmit corresponding signals to subsystem modules 506. At Step 546, system 500 processes data signals at each of the subsystem modules, thus generating corresponding subsystem health signals. Preferably, this processing is performed by each subsystem independent of the processing performed by the other subsystems to initially determine whether any of the individual subsystems is exhibiting a characteristic that will cause it to fail and what is, if known, the "time-to-fail" and the mechanism of failure (e.g., wear, cracking, etc.). The individual subsystem modules 506, in Step 548, then determine whether that subsystem requires maintenance and how time critical that maintenance is by assessing the subsystem health signals generated thereby. In the event that timely maintenance is required, program 540 executes Step 550 to generate a notification signal and, at Step 551 store the notification data and transmit the notification signal to an indicator unit (510 in FIG. 12) which responds by conveying warning information to the user. In response, the user can bring the vehicle into a service station for maintenance if the problem requires immediate attention. Otherwise, system 500 will indicate, for example, how long the user can operate the vehicle before maintenance will be required.

Whether the subsystem requires maintenance based on an evaluation of subsystem health signals or not, the subsystem health assessment signals are then transmitted to the master diagnostic module at Step 552. By processing the subsystem health assessment signals, master diagnostic module 508 generates an overall vehicle health signal at Step 554. At this point, program 540 again determines whether any subsystem requires maintenance, preferably based on the overall vehicle health signal, at Step 556. If so, master diagnostics module 508 generates a notification signal at Step 558. At Step 559, the notification data is stored and the notification signal is transmitted to the indicator unit which responds by conveying the warning information to the user. Step 556 preferably includes utilizing a model 530 to efficiently determine whether it is necessary to take the vehicle out of service for maintenance or when it will become critical to provide maintenance.

Continuing, whether or not the master diagnostics module determines that a subsystem requires immediate maintenance, program 540 executes Step 560 to generate and store a trend analysis based on the subsystem data signals, subsystem health signals, and/or the overall vehicle health signal. The program then executes Step 562 to generate and store a trend analysis based on user input, subsystem health signals and/or the overall vehicle health signal. This trend analysis allows program 540 to accurately plan a maintenance schedule for that vehicle such that maintenance is not performed before it is absolutely necessary, yet is performed prior to any catastrophic event. This trend analysis is preferably determined by the central terminal after the health signals and/or raw data 13 is transmitted thereto.

Alternatively, this trend analysis may be performed by master diagnostics module 508 on-board the vehicle. For example, master diagnostics module 508, and in one preferred embodiment is implemented as a swappable module that can be removed from vehicle 502 and placed in, for example, a docking station at the central terminal (e.g., a service station) as described above.

Figure 15:
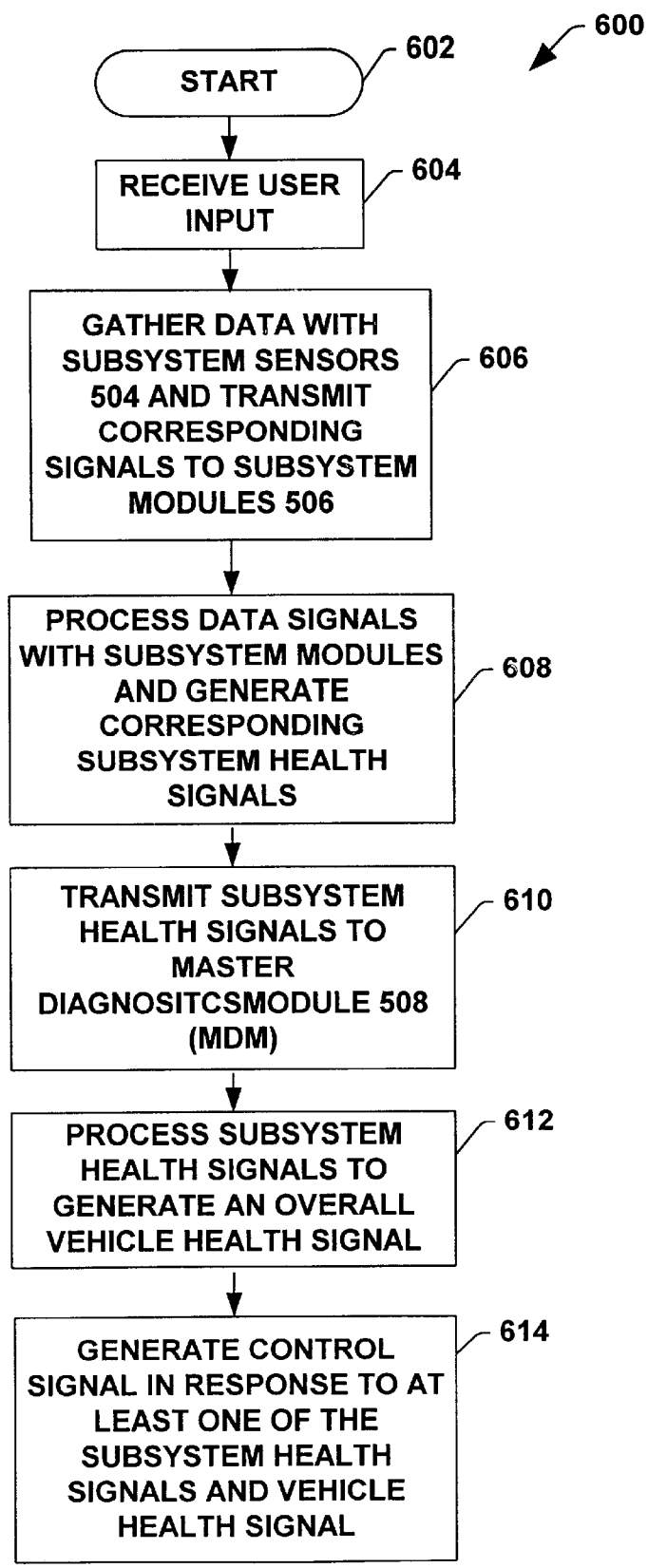
FIG. 15 is a flow chart showing an alternate embodiment of the general operation of the vehicle diagnostics system of the preferred embodiment of the present invention.

An alternative embodiment of the general operation of system 500 is shown at FIG. 15, wherein a control feature has been added. After initialization and start-up at Step 602, program 600 receives user input, if any, which, for example, may be indicative of particular expected vehicle operating conditions at Step 604 or possibly the time until next available maintenance operations. Next, at Step 606, program 600 prompts sensors to gather data and transmit corresponding signals to subsystem modules. Then, at Step 608 subsystem modules process the data signals and generate corresponding subsystem health signals that are indicative of, for example, whether the subsystem, or a component therein, requires maintenance. Next, at Step 610, the subsystem health signals are transmitted to the master diagnostics module. The master diagnostics module then processes the subsystem health signals to generate an overall vehicle health signal at Step 612. As stated previously, a model is preferably embedded in the memory of the master diagnostics module for accurately and reliably assessing the health of both individual vehicle subsystems and the overall health of the vehicle. These models can be both qualitative and quantitative models.

In response to the subsystem health signals and/or the vehicle health signals, system 500 generates a control signal at Step 614, to alter the operation of one of the subsystems in such a way as to maximize its useful life and minimize maintenance requirements. For example, if the rear differential of a vehicle is running at excessively high temperatures, a control signal may be generated to change the transmission speed at which the transmission automatically shifts gears, i.e., to a lower than normal speed. By doing so, system 500 will operate to reduce the amount of oil sheer and mixing which contributes to heat buildup in the differential. Notably, implementing such control will often times yield positive effects on other subsystems 506 as well. For instance, in this example, heat generation at the bearings may also be reduced. This may be done at the expense of less efficient operation (e.g., increased fuel consumption), however, the lifetime of a critical component may be extended and a catastrophic failure avoided.

In another example, if a sensor detects high stress or wear due to loading on the gears of transmission components, system program 600 can cause, via generation of a control signal at Step 614, the vehicle transmission to shift in a delayed fashion (i.e., at a higher RPM) during acceleration to reduce gear loading. Alternatively, the controller could alter the engine's torque output by de-tuning the engine or limiting the acceleration rate so as to not exceed a critical transmission or drive train load threshold, thus extending transmission life. Yet another example concerns the system's capability of detecting engine vibration and particular engine vibration at a critical frequency due to, for example, loose mounting. In response, system operation program 600 generates a control signal to change the RPM associated with transmission shifting to accelerate or decelerate "through" that critical frequency.

Notably, other types of processing may also be implemented with, for example, master diagnostics module 508, such as wavelet analysis, neural net classifiers, advanced filtering, and current signature techniques, to further facilitate accurate and reliable diagnostics and prognostics computations and analysis.

Overall, vehicle diagnostics system 500 (FIG. 12) is capable of identifying critical cost and wear factors such that system monitoring and trend analysis can be efficiently implemented to yield an overall optimum maintenance schedule for the vehicle. In additional, central terminal 524 can be utilized to receive and process information regarding an entire fleet of vehicles so as to intelligently determine which vehicle should be brought in and for what service and at what time, thus minimizing vehicle downtime and overall operating costs. Factors such as operators, routes, loads and even time of day may be analyzed to establish cost/performance critical parameters and to optimize transportation performance and vehicle scheduling.

In addition, master diagnostics module 508 preferably includes routines for performing diagnostics on the vehicle diagnostic system 500 itself, thus insuring that all sensors 504 and subsystems 506 are in proper operating condition, etc. Moreover, as stated previously, sensors 504 are preferably intelligent sensors that are capable of setting different parameters for measuring characteristics of different types of environments. For instance, the lubrication sensor may be configured to detect a certain pH of, for example, the lubrication applied to a particular component.

In one brief example, a subsystem 506 includes a lube sensor and a vibration sensor 506 for making an overall subsystem health assessment. In the event that the health assessment indicates that a side wall of a tire is separated, subsystem 506, or master diagnostics module 508, can generate and transmit a subsystem health assessment signal that indicates that the vehicle should not be driven over 60 miles per hour.

By using a hierarchy of intelligence including diagnostics performed at the subsystem and overall vehicle levels, vehicle diagnostics system 500 can intelligently determine when particular subsystems or components therein are about to fail, even when sensors monitoring that particular subsystem or component do not indicate an immediate health concern. To illustrate this aspect of the invention, consider, for example, a bearing that may be exhibiting significant vibration may be considered. The subsystem 506 that is monitoring that bearing may indicate that the bearing is going to last for six more months before maintenance will be required, despite the fact that it is being exposed to significant vibration. However, when that information is processed, for instance, by master diagnostics module 508 in conjunction with an appropriate system model 530, module 508 may determine that the particular vibration detected is exerting undue stress on the steering column or steering box such that maintenance will be required prior to the expiration of the six month period. By efficiently and intelligently implementing models 530 in memory 528 of master diagnostics module 508, system 500 can derive a maintenance schedule that is not based on merely a preventive maintenance schedule (such as change the oil every 3000 miles), but rather based on an overall health assessment of vehicle subsystems and components therein.

Another example exhibiting how the present system provides advantages over known systems concerns the transmission of health assessment signals to central terminal 524 via communication link 522. System 500 may suddenly detect that a wheel bearing is dry or has a seal that has failed, thus permitting contaminants to disrupt the operation of the wheel. As this condition is detected during a trip, master diagnostics module 508 can transmit an appropriate health assessment signal via communication link 522 (e.g., a radio link) to a dispatcher, indicating that the vehicle is not equipped to complete the planned trip. With this information, the dispatcher can thereafter plan job completion and vehicle re-routing and maintenance accordingly.

As indicated previously, system 500 may use an input terminal 509 that permits the user to indicate requirements for a particular trip, such as that the vehicle needs to operate maintenance free for the next 8000 miles. In response, system 500 can perform a diagnostics/prognostics evaluation to determine what maintenance will be required to achieve the operational goals indicated by the user. This evaluation may be based on stored system diagnostics and prognostics system models the user input.

Rather than typical preventive maintenance performed by most vehicle users, vehicle diagnostics and prognostics system 500 operates in an essentially proactive fashion. Where preventive maintenance dictates a specific number of miles change or repair a component, system 500 considers actual subsystem and vehicle health by determining when a component will require maintenance. This will help to optimize transportation routes, reduce maintenance costs, increase each vehicle's "productive" operating time, avoid unexpected and catastrophic failures, and help the environment by avoiding unnecessary fluid (oil, transmission coolant, etc.) changes.

Although the present invention is described in terms of land-based vehicles, the invention may readily be extended to other complex, dynamic systems such as aircraft and ships. There is a corresponding need to diagnose critical subsystems in these examples and the subsystems are inherently coupled in the operation of these dynamic systems.

Although the best mode contemplated by the inventors of carrying out the present invention is disclosed above, practice of the invention is not limited thereto. It will be manifest that certain various additions, modifications and rearrangements of the features of the present invention may be made without deviating from the spirit and scope of the underlying inventive concept.

What is claimed is:

1. A diagnostic/prognostics system for collecting and processing data relating to a plurality of subsystems of a dynamic system, the system comprising:
    a plurality of sensors, each sensor gathering data and generating a data signal indicative of the health of a corresponding one of the subsystems;
    a plurality of subsystem modules each electrically coupled to at least one corresponding sensor for generating a subsystem health signal in response to corresponding ones of the data signals, wherein one of the subsystem modules determines the lubrication health of the lubrication of the corresponding subsystem; and
    a master diagnostics module electrically coupled to said subsystem modules, said master diagnostics module generating a system health signal in response to the subsystem health signals.

2. The diagnostics/prognostics system of claim 1, further including a central terminal coupled to said master diagnostics module via a communications link to facilitate further processing of at least one of the group comprising the subsystem health signals and the system health signal.

3. The diagnostics/prognostics system of claim 2, wherein the further processing includes generating a trend analysis, said trend analysis being indicative of a prediction regarding when one of the subsystems will require maintenance.

4. The diagnostics/prognostics system of claim 1, wherein each said sensor is integral with an associated component of a corresponding one of the subsystems.

5. The diagnostics/prognostics system of claim 2, wherein said master diagnostics module is a plug-in module and the communications link is a docking station disposed at the central terminal.

6. The diagnostics/prognostics system of claim 4, wherein said central terminal includes a host computer for processing at least one member of the group consisting of the subsystem health signals and the system health signal so as to generate a maintenance schedule that is indicative of when at least one of the system subsystems will require maintenance.

7. The diagnostics/prognostics system of claim 2, wherein the communications link is a wireless link.

8. The diagnostics/prognostics system of claim 6, wherein said master diagnostics module includes a transmitter and the wireless link is a paging network.

9. The diagnostics/prognostics system of claim 1, wherein said master diagnostics module includes a memory having an embedded model to facilitate generating the system health signal.

10. The diagnostics/prognostics system of claim 9, wherein said embedded model facilitates assessment of the health of one of the subsystems based on the health of at least one other of the subsystems.

11. The diagnostics/prognostics system of claim 1, wherein said system is a vehicle.

12. The diagnostics/prognostics system of claim 1, wherein said system is a ship.

13. The diagnostics/prognostics system of claim 1, wherein said system is an airplane.

14. The diagnostics/prognostics system of claim 1, wherein one of said subsystem health signals is based on a corresponding one of the data signals indicative of vibration.

15. The diagnostics/prognostics system of claim 1, wherein the sensors include a lubrication health sensor disposed within one of the engine, the transmission, the bearings, the radiator, the differential, and the steering gear box of the system.

16. The diagnostics/prognostics system of claim 1, wherein the sensors include a torque sensor disposed within one of the engine, the transmission, the bearings, the radiator, the differential, and the steering gear box of the system.

17. The diagnostics/prognostics system of claim 1, wherein the master diagnostics module includes a memory, the memory storing design and operating information specific to the system.

18. The diagnostics/prognostics system of claim 1, wherein at least one of said sensors is a microviscosity sensor that senses the viscosity of a fluid, and includes
    at least one sensing element exposed to the fluid, said at least one sensing element adapted to be oscillated over a range of frequencies;
    wherein the viscosity of the fluid is determined as a function of the power required to maintain an oscillation of said at least one sensing element at a predetermined frequency.

19. The diagnostics/prognostics system of claim 1, wherein at least one of said sensors comprises a multi-element sensor system that includes
    at least two sensors, each sensor adapted to collect data relating to a fluid;
    a data fusion processor operatively coupled to said at least two sensors, said data fusion processor processing said fluid data to at least compensate for fragmentation of information attributed to using the at least two sensors.

20. The diagnostics/prognostics system of claim 19, wherein said at least two sensors are integrated onto a semiconductor base.

21. The diagnostics/prognostics system of claim 1, wherein at least one of said sensors comprises a wear sensor that includes
an optical fiber for transmitting light from a light source, the optical fiber being embedded in the article; and
wherein the interferometric system provides the processor with information relating to wear of the optical fiber, and the processor determines wear of the article based on the information.

22. A vehicle diagnostics/prognostics system for collecting data relating to a plurality of subsystems of a vehicle, the system comprising:
a plurality of sensors for gathering data and generating corresponding data signals indicative of the health of associated ones of the subsystems, a first one of the sensors being disposed within a first vehicle subsystem and a second one of the sensors being disposed within a second vehicle subsystem;
a plurality of subsystem modules electrically coupled to associated ones of the sensors, a first one of the subsystem modules being coupled to the first sensor and a second one of the subsystem modules being coupled to the second sensor, said subsystem modules generating first and second subsystem health signals in response to corresponding ones of the data signals; and
a master diagnostics module electrically coupled to said subsystem modules to receive and process at least one member of the group consisting of the data signals and the subsystem health signals so as to facilitate rendering a health assessment of the vehicle.

23. The vehicle diagnostics/prognostics system of claim 22, wherein the subsystem modules include a combination of at least two of the following: a drive train health module, an engine health module, a suspension system health module, and a rear differential health module.

24. The vehicle diagnostics/prognostics system of claim 22, wherein the health assessment is a first health assessment of the first vehicle subsystem, the first health assessment being based on the second health signal.

25. The vehicle diagnostics/prognostics system of claim 22, wherein at least one of said sensors is a microviscosity sensor that senses the viscosity of a fluid, and includes
at least one sensing element exposed to the fluid, said at least one sensing element adapted to be oscillated over a range of frequencies;
wherein the viscosity of the fluid is determined as a function of the power required to maintain an oscillation of said at least one sensing element at a predetermined frequency.

26. The vehicle diagnostics/prognostics system of claim 22, wherein at least one of said sensors comprises a multi-element sensor system that includes
at least two sensors, each sensor adapted to collect data relating to a fluid;
a data fusion processor operatively coupled to said at least two sensors, said data fusion processor processing said fluid data to at least compensate for fragmentation of information attributed to using the at least two sensors.

27. The vehicle diagnostics/prognostics system of claim 26, wherein said at least two sensors are integrated onto a semiconductor base.

28. The vehicle diagnostics/prognostics system of claim 22, wherein at least one of said sensors comprises a wear sensor that includes
an optical fiber for transmitting light from a light source, the optical fiber being embedded in the article; and
wherein the interferometric system provides the processor with information relating to wear of the optical fiber, and the processor determines wear of the article based on the information.

29. A method of determining when a vehicle having a plurality of subsystems requires maintenance, the method comprising the steps of:
using a plurality of sensors to gather data indicative of the health of corresponding ones of the subsystems, and generate corresponding data signals based on the health data;
providing a plurality of subsystem modules, each subsystem module being associated with a corresponding ones of the subsystems and being electrically coupled to a corresponding one of the sensors wherein one of the subsystem modules determines the lubrication health of the corresponding subsystem;
generating, with the subsystem modules, subsystem health signals in response to corresponding ones of the data signals;
providing a master diagnostics module electrically coupled to the subsystem modules; and
generating, with the master diagnostics module and in response to the subsystem health signals, a vehicle health signal.

30. The method according to claim 29, further comprising the steps of
determining when the vehicle requires maintenance in response to at least one member of the group consisting of the subsystem health signals and the vehicle health signal; and
determining what maintenance is required and when the maintenance is required to meet optimization criteria.

31. The method according to claim 30, wherein said determining step is performed based on a maintenance model embedded in a memory of the master diagnostics module.

32. The method according to claim 29, further comprising the step of receiving user input data indicative of an operational parameter, wherein said generating the vehicle health signal is based on the user input data.

33. The method according to claim 32, wherein the operational parameter is one of travel distance parameter, a load parameter, and a terrain parameter.

34. A method of determining when a vehicle having a plurality of subsystems requires maintenance, the method comprising the steps of:
generating data signals with a plurality of sensors, the sensors being associated with corresponding ones of the subsystems;
transmitting the data signals to corresponding ones of a plurality of subsystem modules;
generating, with the subsystem modules, subsystem health signals in response to the corresponding data signals;
transmitting the subsystem health signals to a central terminal at a location remote from the vehicle, the central terminal having a host computer for processing the subsystem health signals;
determining, with the host computer and in response to the subsystem health signals, whether the vehicle requires maintenance; and
wherein said determining step is based on a predetermined vehicle diagnostics/prognostics model.

35. The vehicle diagnostics/prognostics system of claim 34, wherein said transmitting the subsystem health signals step includes activating a radio transmitter associated with corresponding ones of the subsystem modules.

36. A method of determining when a vehicle having a plurality of subsystems requires maintenance, the method comprising the steps of:
generating data signals with a plurality of sensors, the sensors being associated with corresponding ones of the subsystems;
transmitting the data signals to corresponding ones of a plurality of subsystem modules;
generating, with the subsystem modules, subsystem health signals in response to the corresponding data signals;
transmitting the subsystem health signals to a master diagnostics, wherein said master diagnostics module is a swappable plug-in module and said transmitting the subsystem health signals and the vehicle health signal steps include removing the plug-in module and placing the plug-in module in a docking station disposed at the central terminal, the docking station being configured to mechanically receive the plug-in module;
generating, with the master diagnostics module, a vehicle health signal in response to the subsystem health signals;
transmitting at least one member of the group consisting of the subsystem health signals and the vehicle health signal to a central terminal at a location remote from the vehicle, the central terminal having a host computer; and
determining, with the host computer and in response to the at least one signal, whether the vehicle requires maintenance.

37. The method according to claim 36, wherein said determining step is based on a predetermined vehicle diagnostics/prognostics model.

38. The method according to claim 36, wherein said transmitting the subsystem health signals step includes activating a radio transmitter associated with corresponding ones of the subsystem modules.

39. The method according to claim 36, further comprising the step of predicting a trend, with the host computer and in response to at least one of a group consisting of the subsystem health signals and the vehicle health signals, the trend indicative of when one of the vehicle subsystems will be generally near failure such that maintenance will be warranted.

40. A vehicle diagnostics/prognostics system for collecting and processing data relating to a plurality of subsystems of a vehicle, the system comprising:
a plurality of subsystem modules for receiving health assessment information associated with each of the subsystems and generating corresponding subsystem health signals based on the health assessment information; and
a master diagnostics module electrically coupled to said subsystem modules and including a memory having a health assessment model embedded in the memory, said master diagnostics module generating a vehicle health assessment based on said health assessment model and in response to the subsystem health signals.

41. The diagnostics/prognostics system of claim 40, wherein said master diagnostics module includes a user input for receiving an operating parameter.

42. The diagnostics/prognostics system of claim 41, wherein the vehicle health assessment is based on the operating parameter.

43. The diagnostics/prognostics system of claim 42, wherein the operating parameter is one of a group consisting of an average speed of the vehicle and a travel distance.

44. A vehicle diagnostics/prognostics system for collecting and processing data relating to a plurality of subsystems of a vehicle, the system comprising:
a plurality of sensors, each sensor gathering data and generating a data signal indicative of the health of a corresponding one of the subsystems;
a plurality of subsystem modules each electrically coupled to at least one corresponding sensor for generating a subsystem health signal in response to corresponding ones of the data signals wherein one of the subsystem modules determines the lubrication health of the lubrication corresponding system;
a master diagnostics module electrically coupled to said subsystem modules, said master diagnostics module generating a vehicle health signal in response to the subsystem health signals; and
a controller to generate a control signal in response to at least one of a group consisting of the subsystem health signals and the vehicle health signal, the control signal causing an operation parameter of at least one of the vehicle subsystems to change.

* * * * *